US012724017B2

(12) United States Patent
Postrel et al.

(10) Patent No.: US 12,724,017 B2
(45) Date of Patent: Sep. 1, 2026

(54) APPARATUS AND METHOD FOR MEASURING VOLATILE ORGANIC COMPOUNDS IN A SPECIMEN TO DETECT THE PRESENCE OF DISEASES

(71) Applicant: VOC Health Inc., Miami Beach, FL (US)

(72) Inventors: Richard Postrel, Miami Beach, FL (US); Ian Hunter, Lincoln, MA (US); Raymond Catania, Palm Bay, FL (US); Christine Bralich, Satellite Beach, FL (US); Kenan Dunton, Cocoa, FL (US)

(73) Assignee: VOC Health Inc., Miami Beach, FL (US)

( * ) Notice: Subject to any disclaimer, the term of this patent is extended or adjusted under 35 U.S.C. 154(b) by 0 days.

(21) Appl. No.: 19/336,619

(22) Filed: Sep. 23, 2025

(65) Prior Publication Data

US 2026/0092906 A1 Apr. 2, 2026

Related U.S. Application Data

(63) Continuation of application No. 19/245,282, filed on Jun. 21, 2025, now Pat. No. 12,461,081.

(Continued)

(51) Int. Cl.
*G01N 33/00* (2006.01)
*B01L 1/02* (2006.01)
*B01L 5/02* (2006.01)

(52) U.S. Cl.
CPC ............ *G01N 33/0047* (2013.01); *B01L 1/02* (2013.01); *B01L 5/02* (2013.01)

(58) Field of Classification Search
CPC .......... G01N 33/0047; B01L 1/02; B01L 5/02
See application file for complete search history.

(56) References Cited

U.S. PATENT DOCUMENTS 5,932,482 A 8/1999 Markelov
2004/0162521 A1 8/2004 Bengtsson (Continued)

FOREIGN PATENT DOCUMENTS

EP 0841094 B1 * 11/2003 .......... B01L 3/50825
WO 2021222910 A2 11/2021

OTHER PUBLICATIONS

International Search Report and Written Opinion, PCT/US2025/034689, VOC Health Inc.

(Continued)

*Primary Examiner* — Kathryn Elizabeth Limbaugh
(74) *Attorney, Agent, or Firm* — Sutton Magidoff Barkume LLP

(57) ABSTRACT

An apparatus and method for determining the presence of a disease by analyzing a specimen by providing a vial partially containing the specimen and partially containing a head-space above the specimen, injecting an inert gas into the specimen in the vial to cause bubbling of the gas throughout at least a portion of the specimen such that the gas mixes with volatile organic compounds (VOCs) present in the specimen to create a VOC/gas mixture that is released into the headspace, collecting the VOC/gas mixture from the headspace in the vial, supplying the VOC/gas mixture to a chamber within the apparatus, causing the VOC/gas mixture to pass over a sensor array in proximity to the chamber, the sensor array generating an electrical signal as a function of VOCs detected in the VOC/gas mixture, and processing the electrical signal to determine the presence of a disease in the specimen.

19 Claims, 24 Drawing Sheets

Related U.S. Application Data

(60) Provisional application No. 63/663,360, filed on Jun. 24, 2024.

(56) References Cited

U.S. PATENT DOCUMENTS

| | | | | |
|---|---|---|---|---|
| 2007/0184553 | A1 | 8/2007 | Hartlein et al. | |
| 2016/0266084 | A1* | 9/2016 | Burge | G01N 33/1826 |
| 2022/0050074 | A1* | 2/2022 | Postrel | G01N 27/4146 |
| 2024/0060114 | A1 | 2/2024 | Buse et al. | |

OTHER PUBLICATIONS

6595—Portable Biosensor for Health Monitoring and Diagnosis, Center for Technology Licensing at Cornell University, date unknown.

* cited by examiner

APPARATUS AND METHOD FOR MEASURING VOLATILE ORGANIC COMPOUNDS IN A SPECIMEN TO DETECT THE PRESENCE OF DISEASES

TECHNICAL FIELD

This invention relates generally to the measurement of volatile organic compounds (VOCs) in a bodily specimen or sample such as urine, blood plasma, and body odors, and in particular to an apparatus for measuring VOCs in one or multiple samples simultaneously or consecutively in a precise and efficient manner and then using the measurements to determine if one or more diseases are indicated by the presence of certain VOCs in the specimen.

BACKGROUND OF THE INVENTION

The human body is known to generate certain metabolic responses in order to fight onset of a disease, such as but not limited to cancer. These metabolic responses will produce volatile organic compounds (VOCs), which result in a specific VOC pattern or signature. That is, VOCs produced by the presence of a disease may serve as a biomarker for identification of that disease. Recognition and diagnosis of complex diseases may therefore be possible by analyzing VOCs released in urine or other bodily fluids. Thus, in order to provide early disease detection, it is desired to provide a system that is able to analyze VOCs contained in a specimen obtained from a person (such but not limited to their urine) and analyze the captured VOCs in order to ascertain the presence of a related disease.

SUMMARY OF THE INVENTION

The present invention is an apparatus and method of use for collecting, measuring and analyzing VOCs obtained from a specimen sample in a robust, efficient, and reliable manner, generating a signature or pattern based on the measured VOCs, and analyzing the generated VOC signature against a library of known VOC signatures to determine the presence of disease(s).

As described in further detail below, the present system includes an apparatus that enables measurement of VOCs in up to four different specimen samples that have been collected into a vial(s) from one or more patients. An inert gas, such as but not limited to Argon, is fed into the apparatus from an external supply, where it is optionally heated to a desired temperature known to be optimal for obtaining and measuring the VOCs. After heating, the gas is routed through a manifold to four independent channels for measurement purposes.

In each measurement channel, the gas is injected into the specimen in each vial to cause bubbling of the gas throughout at least a portion of the specimen such that the gas mixes with VOCs present in the specimen to create a VOC/gas mixture that is released into the headspace above the specimen in the vial. Then, the VOC/gas mixture is collected from the headspace in the vial and sent to a vortex chamber for analysis.

In the vortex chamber, the VOC/gas mixture is swirled around in a vortex-like manner and continually passes over a sensor array in proximity to the vortex chamber, where the VOCs from the inert VOC/gas mixture are detected by the sensor array and an electrical signal is generated by the sensor array that is a function of the detected VOCs. The electrical signal is sent to a computer system for storage and analysis. A signature pattern is generated from the electrical signal indicative of the VOC content in the VOC/gas mixture that has been detected by the sensor array in the chamber. The generated signature pattern is analyzed against a library of previously stored signature patterns, wherein the analysis may indicate the presence of a disease that has been previously associated with a known stored VOC signature pattern.

Thus, with respect to each individual measurement channel in the apparatus, provided is a method of determining the presence of a disease by analyzing a specimen by providing in the apparatus a vial(s) partially containing the specimen and partially containing a headspace above the specimen; injecting an inert gas into the specimen in the vial to cause bubbling of the gas throughout at least a portion of the specimen such that the gas mixes with volatile organic compounds (VOCs) present in the specimen to create a VOC/gas mixture that is released into the headspace in the vial, collecting the VOC/gas mixture from the headspace in the vial and supplying it to a chamber within the apparatus, causing the VOC/gas mixture to pass over a sensor array in proximity to the chamber so that the sensor array generates an electrical signal as a function of VOCs detected in the VOC/gas mixture, and processing the electrical signal to determine the presence of a disease in the specimen by, for example, analyzing the electrical signal against a library of stored VOC signatures, each of the stored VOC signatures associated with a disease to determine the presence of a disease in the specimen.

In a first embodiment, the vial includes a removable vial cap that has a gas input passageway coupled to a first side of a gas injection valve in the cap and an injection passageway coupled to a second side of the gas injection valve. The injection passageway has at least one injection passageway opening extending below the headspace and into the specimen. In this embodiment, the step of injecting an inert gas into the specimen in the vial includes inserting an injection tube into the gas input passageway to make contact with and urge against the first side of the gas injection valve to cause the gas injection valve to open, and injecting the gas into the specimen via the open gas injection valve and through the at least one injection passageway opening.

Optionally, the injection passageway may have a multiplicity of injection passageway openings located throughout a portion of the injection passageway that extends into the specimen, such that the inert gas injected via the open gas injection valve passes through the multiplicity of injection passageway openings into the specimen, causing a micro-bubbling of the inert gas within the specimen that results in the VOC/gas mixture. The injection passageway may also include a diffusion stone that extends into the specimen, such that the inert gas injected via the injection needle passes through the diffusion stone into the specimen, causing a micro-bubbling of the inert gas within the specimen that results in the VOC/gas mixture.

In this first embodiment, the vial cap also has has a gas output passageway coupled to a first side of a gas collection valve in the cap and a collection passageway coupled to a second side of the gas collection valve, the collection passageway adjoining the headspace but not extending into the specimen. Here, the step of collecting the VOC/gas mixture from the headspace comprises inserting a collection tube into the gas output passageway to make contact with and urge against the first side of the gas collection valve to cause the gas collection valve to open, and collecting the VOC/gas mixture from the headspace via the open gas injection valve.

In a second embodiment, rather than using valves, the vial includes a removable vial cap that has a penetrable membrane and an injection passageway with at least one injection passageway opening extending below the headspace and into the specimen. In this second embodiment, the step of injecting an inert gas into the specimen in the vial includes inserting an injection needle through the membrane such that the tip of the injection needle extends into the injection passageway, and injecting the gas into the specimen via the tip of the injection needle and through the at least one injection passageway opening.

Optionally, the injection passageway may have a multiplicity of injection passageway openings located throughout a portion of the injection passageway that extends into the specimen, such that the inert gas injected via the injection needle passes through the multiplicity of injection passageway openings into the specimen, causing a micro-bubbling of the inert gas within the specimen that results in the VOC/gas mixture. The injection passageway may also include a diffusion stone that extends into the specimen, such that the inert gas injected via the injection needle passes through the diffusion stone into the specimen, causing a micro-bubbling of the inert gas within the specimen that results in the VOC/gas mixture.

In this second embodiment, the vial cap also has a collection passageway adjoining the headspace but not extending into the specimen. Here, collecting the VOC/gas mixture from the headspace includes inserting a collection needle through the membrane of the cap such that the tip of the collection needle extends into the collection passageway, and collecting the VOC/gas mixture from the headspace via the tip of the collection needle.

In a third embodiment, which also uses needles and a membrane instead of valves in the cap, the injection passageway and collection passageway are omitted. In this case, the injection needle is inserted through the membrane such that the tip of the injection needle extends below the headspace and directly into the specimen, and the gas is injected directly into the specimen via the tip of the injection needle. In this third embodiment, the collection needle is inserted through the membrane such that the tip of the collection needle extends into the headspace and not into the specimen, and the VOC/gas mixture is collected from the headspace via the tip of the collection needle.

Preferably, external gas tanks are used, including an external gas supply tank that is coupled to the apparatus for supplying the inert gas, as well as an external waste collection tank located exterior to the apparatus for storing the VOC/gas mixture when it exits the apparatus after passing over the sensor array in proximity to the chamber.

Optionally in some embodiments, prior to injecting the inert gas into the specimen in the vial, the inert gas flows through a first mass flow controller within the apparatus, the first mass flow controller providing precise control of the flow rate of the inert gas injected into the vial. Additionally, the flow of inert gas may first be divided into two paths: a first path that couples to the first mass flow controller, and a second path that couples to a second mass flow controller. In this case, the output of the second mass flow controller is mixed with the VOC/gas mixture collected from the vial prior to being supplied to the chamber, and the first mass flow controller and the second mass flow controller are each operated to control their respective flow rates and thus the mixing of the output of the second mass flow controller relative to the VOC/gas mixture from the vial prior to being supplied to the chamber. This enables the relative concentration of VOCs being supplied to the chamber to be selectively controlled. Optionally, the flow of the VOC/gas mixture into the chamber may also be controlled with a solenoid valve.

In some embodiments, a pneumatic cylinder may be coupled to the exit port of the chamber and operated to control pressure within the chamber and thus control the supply of the VOC/gas mixture through the chamber. For example, the pneumatic cylinder may be used to de-pressurize the chamber and draw in the VOC/gas mixture from the vial at a desired flow rate.

The VOC/gas mixture passes over a sensor array in proximity to the chamber and is caused to continually swirl around in the chamber and pass over the sensor array, for example by creating a vortex within the chamber in order to cause the VOC/gas mixture to continually swirl around the chamber and pass over the sensor array for a controlled duration of time, as desired. Optionally, a shutter may be provided between the chamber and the sensor array and operated to control flow of the VOC/gas mixture within the chamber to the sensor array. For example, the shutter could be closed electronically to keep the VOC/gas mixture from contacting the sensor array until such time that the shutter is opened.

The methods discussed above are accomplished with this invention by an apparatus for determining the presence of a disease by analyzing a specimen, which includes a housing, a gas input valve for interconnecting a supply of inert gas to the housing, and a gas output valve for supplying the processed VOC/gas mixture to an external waste tank. Within the housing is a manifold adapted to divide a supply of inert gas input via the gas input valve into a first gas line supplied to a first mass flow controller and a second gas line supplied to a second mass flow controller. The first mass flow controller is coupled to the first gas line output from the manifold, and the second mass flow controller is coupled to the second gas line output from the manifold. A vial is provided that partially contains the specimen and partially contains a headspace above the specimen.

A gas injection device is coupled to an output of the first mass flow controller, such that the gas injection device injects gas from the first mass flow controller into the vial and causes gas provided from the first mass flow controller to bubble throughout at least a portion of the specimen to cause the gas to mix with volatile organic compounds (VOCs) present in the specimen and create a VOC/gas mixture that is released into the headspace in the vial. A gas collection device collects the VOC/gas mixture from the headspace in the vial and feeds the VOC/gas mixture to a first input of a mixing tee.

The mixing tee mixes/combines the VOC/gas mixture from the gas collection device with gas received directly from the output of the second mass flow controller. A system controller computer is connected to the first mass flow controller and the second mass flow controller and is programmed to control a flow rate of the gas through the first mass flow controller and a flow rate of the gas through the second mass flow controller in order to control the concentration of VOCs being supplied by the output of the mixing tee.

A printed circuit board houses a sensor array in proximity to a chamber which is coupled to the output of the mixing tee. As such, the VOC/gas mixture output by the mixing tee passes over the sensor array in proximity to the chamber, which generates an electrical signal as a function of VOCs detected in the VOC/gas mixture.

The system controller is further programmed to process the electrical signal to determine the presence of a disease in the specimen by analyzing the electrical signal generated by the sensor array with respect to a library of stored VOC signatures, each of the stored VOC signatures associated with a disease to determine the presence of a disease in the specimen.

In a first embodiment, the gas injection device includes a vial cap removably coupled to the vial, the vial cap having a gas input passageway coupled to a first side of a gas injection valve in the cap and an injection passageway coupled to a second side of the gas injection valve. The injection passageway has at least one injection passageway opening extending below the headspace and into the specimen. The gas injection device also includes an injection tube coupled to the output of the first mass flow controller, such that, when the injection tube is inserted into the gas input passageway and makes contact with and urges against the first side of the gas injection valve, the gas injection valve is caused to open and the gas is injected into the specimen via the open gas injection valve and through the at least one injection passageway opening.

Optionally, the injection passageway may have a multiplicity of injection passageway openings located throughout a portion of the injection passageway that extends into the specimen, such that the inert gas injected via the open gas injection valve passes through the multiplicity of injection passageway openings into the specimen, causing a micro-bubbling of the inert gas within the specimen that results in the VOC/gas mixture. The injection passageway may also include a diffusion stone that extends into the specimen, such that the inert gas injected through the diffusion stone into the specimen causes a micro-bubbling of the inert gas within the specimen that results in the VOC/gas mixture.

In this first embodiment, the gas collection device also has a gas output passageway in the vial cap coupled to a first side of a gas collection valve in the vial cap and a collection passageway in the vial cap coupled to a second side of the gas collection valve. The collection passageway adjoins the headspace but does not extend into the specimen, and a collection tube is coupled to the first input of the mixing tee. When the collection tube is inserted into the gas output passageway and makes contact with and urges against the first side of the gas collection valve, the gas collection valve is caused to open, and the VOC/gas mixture is collected from the headspace via the open gas collection valve.

In a second embodiment, rather than using valves, the gas injection device includes a vial cap removably coupled to the vial, the vial cap having a penetrable membrane and an injection passageway with at least one injection passageway opening extending below the headspace and into the specimen. In this case, the gas injection device has an injection needle insertable through the membrane such that the tip of the injection needle extends into the injection passageway, and gas is injected into the specimen via the tip of the injection needle and through the at least one injection passageway opening.

Optionally, the injection passageway has a multiplicity of injection passageway openings located throughout a portion of the injection passageway that extends into the specimen, such that the inert gas injected via the injection needle passes through the multiplicity of injection passageway openings into the specimen, causing a micro-bubbling of the inert gas within the specimen that results in the VOC/gas mixture. Further optionally, the injection passageway has a diffusion stone that extends into the specimen, such that the inert gas injected via the injection needle passes through the diffusion stone into the specimen, causing a micro-bubbling of the inert gas within the specimen that results in the VOC/gas mixture.

In this second embodiment, the vial cap also has a collection passageway adjoining the headspace but not extending into the specimen, and the gas collection device has a collection needle insertable through the membrane such that the tip of the collection needle extends into the collection passageway, such that the VOC/gas mixture is collected from the headspace via the tip of the collection needle.

In a third embodiment, which also uses needles and a membrane instead of valves in the cap, the injection passageway and collection passageway are omitted. In this case, the injection needle is inserted through the membrane such that the tip of the injection needle extends below the headspace and directly into the specimen, and the gas is injected directly into the specimen via the tip of the injection needle. In this third embodiment, the gas collection device has a collection needle insertable through the membrane such that a tip of the collection needle extends the headspace and not into the specimen, such that the VOC/gas mixture is collected from the headspace via the tip of the collection needle.

A needle replacement assembly may be used to make the process of changing needles quicker and safer. The needle replacement assembly includes a cylindrical needle carrier adapted to mount the injection needle and the collection needle (or several pairs thereof in a multi-channel embodiment), the needle carrier having a locking collar with a plurality of lower engagement notches located around a lower rim of the locking collar, and a plurality of upper engagement notches located around an upper rim of the locking collar. A cylindrical cup having a plurality of cup engagement nubs is placed under the needle carrier such that the injection needle(s) and the collection needle(s) are contained within the cup, and the cup engagement nubs are aligned with the lower engagement notches on the lower rim of the locking collar. When the cup is rotated in a first direction with respect to the needle carrier, the cup engagement nubs engage with the lower engagement notches and cause the needle carrier to rotate such that the upper engagement notches disengage from a plurality of fixed engagement nubs, thereby releasing the needle carrier from the apparatus. The process may be reversed to install a new needle replacement assembly with a fresh set of needles.

In some embodiments, the apparatus also has a pneumatic cylinder coupled to the exit port of the chamber, such that the pneumatic cylinder is operated to control pressure within the chamber to control the supply of the VOC/gas mixture through the chamber.

Preferably, the chamber is dome-shaped so as to create a vortex within the chamber in order to cause the VOC/gas mixture to continually swirl around the chamber and pass over the sensor array. Optionally, the apparatus has a shutter provided between the chamber and the sensor array, which is operated to control flow of the VOC/gas mixture within the chamber to the sensor array.

The single measurement channel method described above may be extended to use with multiple channels in the apparatus as follows. Each channel as described above is replicated within the apparatus for n instances, wherein n is the number of channels provided. For example, n=4 in a four-channel apparatus, where four vials are provided, four sets of first and second mass flow controllers, four gas injection devices, four gas collection devices, four pneumatic cylinders, etc. Only a single system controller is needed, however, which may be programmed to control the operating parameters of the four channels accordingly. Gas plumbing components such as mixers, tees, and manifolds are set up to allow the single external gas supply to be fed into each of the four channels, such that the four vials may be processed independently.

Additionally, a vial block and rotating vial block mount are provided on a motorized carousel in the apparatus, which are used to hold the four vials of specimens. In one embodiment, four vials containing four different specimens may be inserted into the vial block, and the four independent measurement channels are then used to extract the VOCs and generate four separate electrical signals, one for each vial placed in the vial block. In this embodiment, specimens may be processed simultaneously (in parallel), at approximately four times the speed of processing four single vials in a single measurement channel consecutively (in series).

In another embodiment, a single vial may be placed on the vial block, which may be rotated around to be sampled by each of the four channels in succession. In this manner, four times as much data is obtained for a single specimen than would otherwise be available with only a single channel. Parameters such as temperature, pressurization, and VOC concentration may be modified for each channel to obtain different types of measurements.

In an alternative embodiment, it is not necessary to provide an inert gas supply to inject into the vial, since the VOCs present in the specimen may naturally disperse into the headspace over the specimen. In that case, the VOC/gas mixture (the gas likely being air) can be caused to enter the chamber for analysis by the sensor array by de-pressurizing the headspace above the specimen in the vial to cause it to flow into the chamber. As such, this method for determining the presence of a disease by analyzing a specimen using an apparatus, includes providing in the apparatus a vial partially containing the specimen and partially containing a headspace above the specimen, de-pressurizing the headspace in the vial, collecting a VOC/gas mixture from the headspace in the vial, supplying the VOC/gas mixture to a chamber within the apparatus, causing the VOC/gas mixture to pass over a sensor array in proximity to the chamber, the sensor array generating an electrical signal as a function of VOCs detected in the VOC/gas mixture, and processing the electrical signal to determine the presence of a disease in the specimen. Here, the step of de-pressurizing the headspace in the vial comprises coupling a pneumatic cylinder to an exit port of the chamber and operating the pneumatic cylinder to de-pressurize the headspace in the vial.

This alternative embodiment apparatus for determining the presence of a disease by analyzing a specimen, includes a housing, a vial partially containing the specimen and partially containing a headspace above the specimen, a gas collection device adapted to collect a VOC/gas mixture from the headspace in the vial and feed the VOC/gas mixture to a chamber, a pneumatic cylinder coupled to an exit port of the chamber, the pneumatic cylinder operable to de-pressurize the headspace in the vial, a system controller computer connected to the pneumatic cylinder, the system controller programmed to control de-pressurization of the headspace in the vial, and a printed circuit board comprising a sensor array in proximity to the chamber, the chamber coupled to the output of the gas collection device, such that the VOC/gas mixture output by the gas collection device passes over the sensor array, the sensor array generating an electrical signal as a function of VOCs detected in the VOC/gas mixture, the system controller further programmed to process the electrical signal to determine the presence of a disease in the specimen.

DETAILED DESCRIPTION OF THE INVENTION

In order to implement the methods and apparatuses of the preferred embodiments, the specimen sample that will be analyzed for VOC content may be acquired in various manners, for example, in a doctor's office, at a hospital, clinic, or anywhere a health care professional is able to do so. In the alternative, a home-based kit may be provided to enable a patient to provide the sample without having to travel. A sample may include but is not limited to urine, blood plasma, body odors via a gauze material rubbed on the patient's hands or a swab, etc. The preferred embodiment for detecting disease(s) in the VOCs is a sample of urine, while the preferred embodiment for detecting infectious disease(s) in the VOCs is a sample of body odor.

Figure 5:
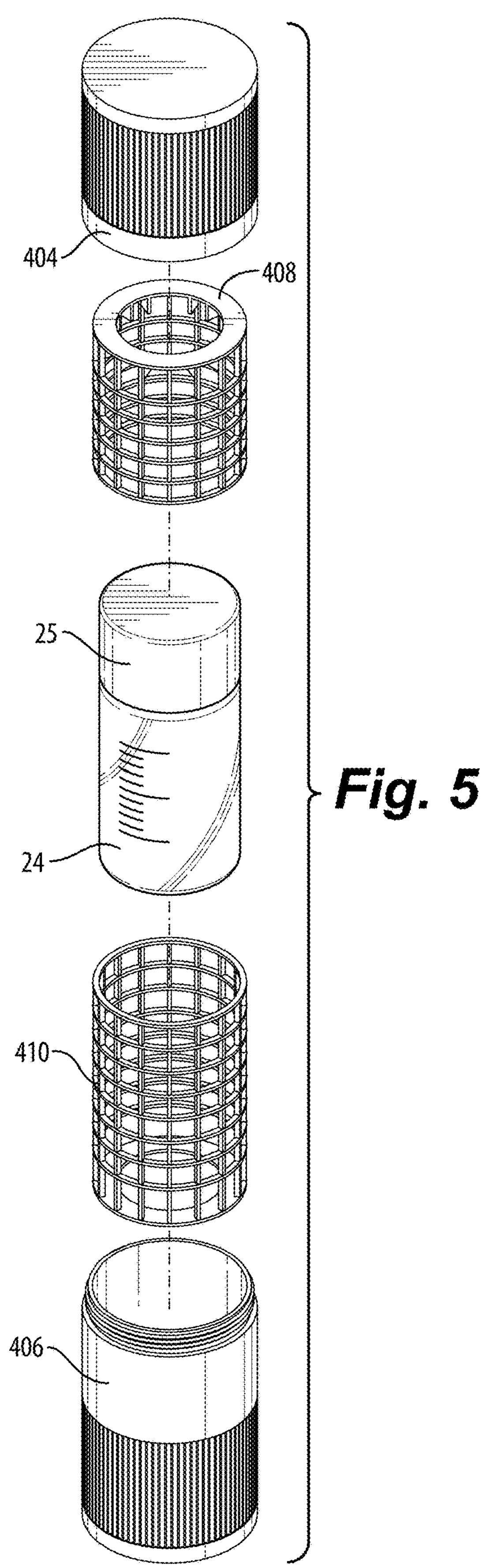
FIG. 5 is an exploded view of a typical specimen vial and the container of FIG. 4.

In order to collect a sample such as urine, a specimen vial 24 is provided, as shown in FIG. 5. The vial 24 is made of translucent or transparent glass and has imprinted thereon a volume gauge 930 to enable easy determination of the volume of specimen sample 920 inside the vial 24 (see FIGS. 19, 20). A generic vial cap 25 is threaded onto mating threads inside the top of the vial, with a tamper proof detection tape optionally used to seal the cap 25 onto the vial 24 to enable detection of any tampering that may occur after the specimen has been deposited in the vial 24.

The vial 24 in the preferred embodiment is capable of containing 40 ml maximum, although typically only 25-30 ml of specimen 920 will be collected. This results in a headspace 922 above the specimen 920 to where VOC/gas mixture will bubble up and percolate during testing.

Figure 1:
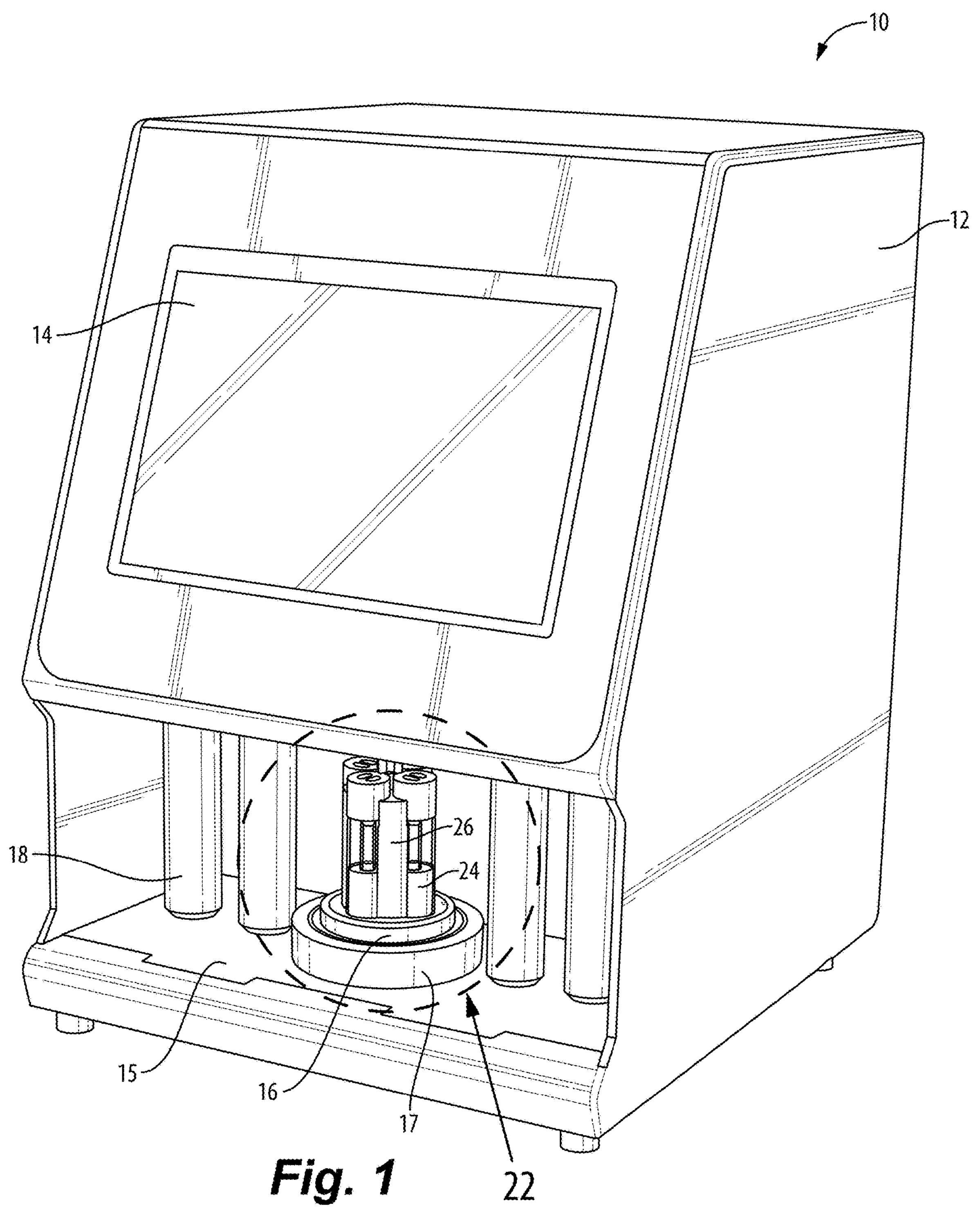
FIG. 1 is a perspective view of a preferred embodiment apparatus of the present invention.

The vial cap 25 as shown in FIG. 5 is a generic cap threaded onto the vial 24 as known in the art and used to contain the specimen sample 920 after it is deposited into the vial 24 by the patient. After the vial 24 has been transported to the site where the testing will be performed, the generic vial cap 25 will be removed by the testing technician and replaced with a specialized cap that has one of several possible gas injection and gas collection devices integrated into the cap, after which the vial(s) 24 will be placed in the apparatus 10 as shown in FIG. 1. The various types of specialized vial caps that may be implemented with this invention depend in how the gas will be injected into the specimen and collected from the headspace. The three embodiments described herein are a valved embodiment, a needle/passageway embodiment, and a needle only embodiment, all of which will be described in further detail below.

The preferred embodiment as described herein is a VOC measurement apparatus 10 as shown in FIG. 1. As also shown in the top-level functional block diagram in FIG. 2, the VOC measurement apparatus 10 includes a housing 12 that is connected via supply gas tubing 112 to an external gas tank 104 and regulator 105, which will provide the apparatus 10 with an inert gas such as but not limited to Argon. External waste tank 106 is also connected to the housing 12 via exit gas tubing 114 to provide external storage of the waste gasses that are produced by the apparatus 10. The gas tubings 112, 114 are connected to the apparatus 10 via input gas valve 108 and output gas valve 110 on the rear of the apparatus 10, respectively (not shown in FIG. 1). Although implementing the gas tank 104 and waste tank 106 externally allows the housing to be relatively small and thus portable, in an alternative embodiment the gas tank 104 and waste tank 106 may be included within (a larger) housing 12 if desired.

Figures 22, 23:
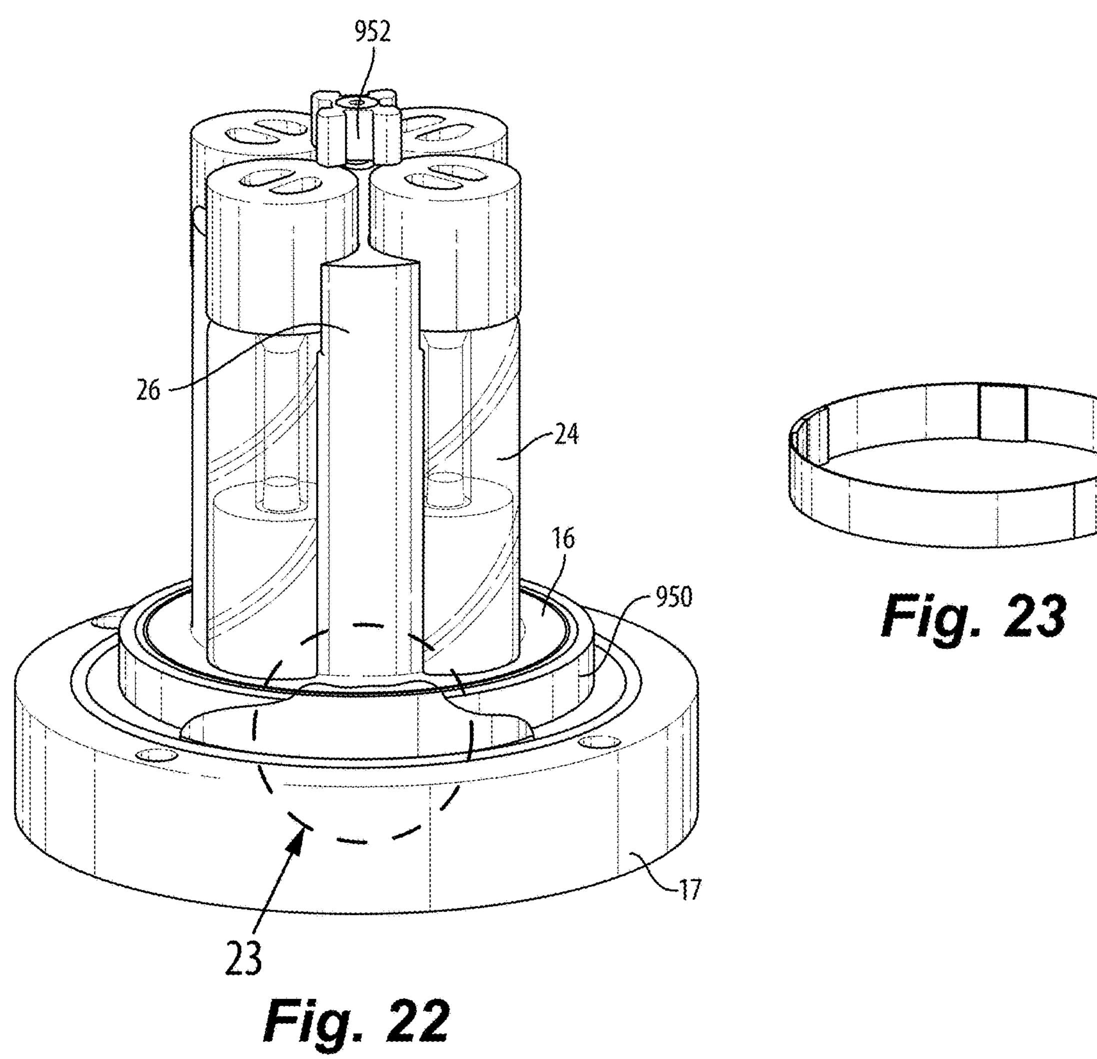
FIG. 22 is a perspective view of a vial block mount and vial block containing four vials, that is mounted to a motorized carousel.
FIG. 23 is an illustration of a flexible heating strip.

Also shown in FIG. 1 is a touchscreen user interface 14, which is used for operator control of a system controller computer 13 (not shown in FIG. 1), which in the preferred embodiment is an APPLE MacMini, although other comparable computers may be used. Below the touchscreen 14 is testing area 15, which has a rotatable motorized carousel 17 onto which a vial block mount 16 and vial block 26 are located. As also shown in FIG. 22, up to four specimen vials 24 to be tested are placed in the vial block 26 that is mounted on the vial block mount 16, such that rotation of the carousel 17 will cause the vials 24 to be rotated from one position to the next. This scenario is useful in situations where a single vial 24 is placed in the vial block 26 for testing in the (first) measurement channel associated with that first position, then rotated one quarter turn and retested in the (second) measurement channel associated with that second position, etc. for testing the specimen in the vial in each of the four measurement channels. This enables the specimen in the vial to be tested under different conditions present in each measurement channel, such as temperature, pressure, duration, etc.

A transparent shield (not shown) is optionally used to cover the testing area 15 during testing to protect the vials 24 and specimens within from any external conditions, if desired. Also shown in FIG. 1 are four pneumatic cylinders 18, one for each of the four measurement channels, all of which will be described in further detail below.

Figure 2:
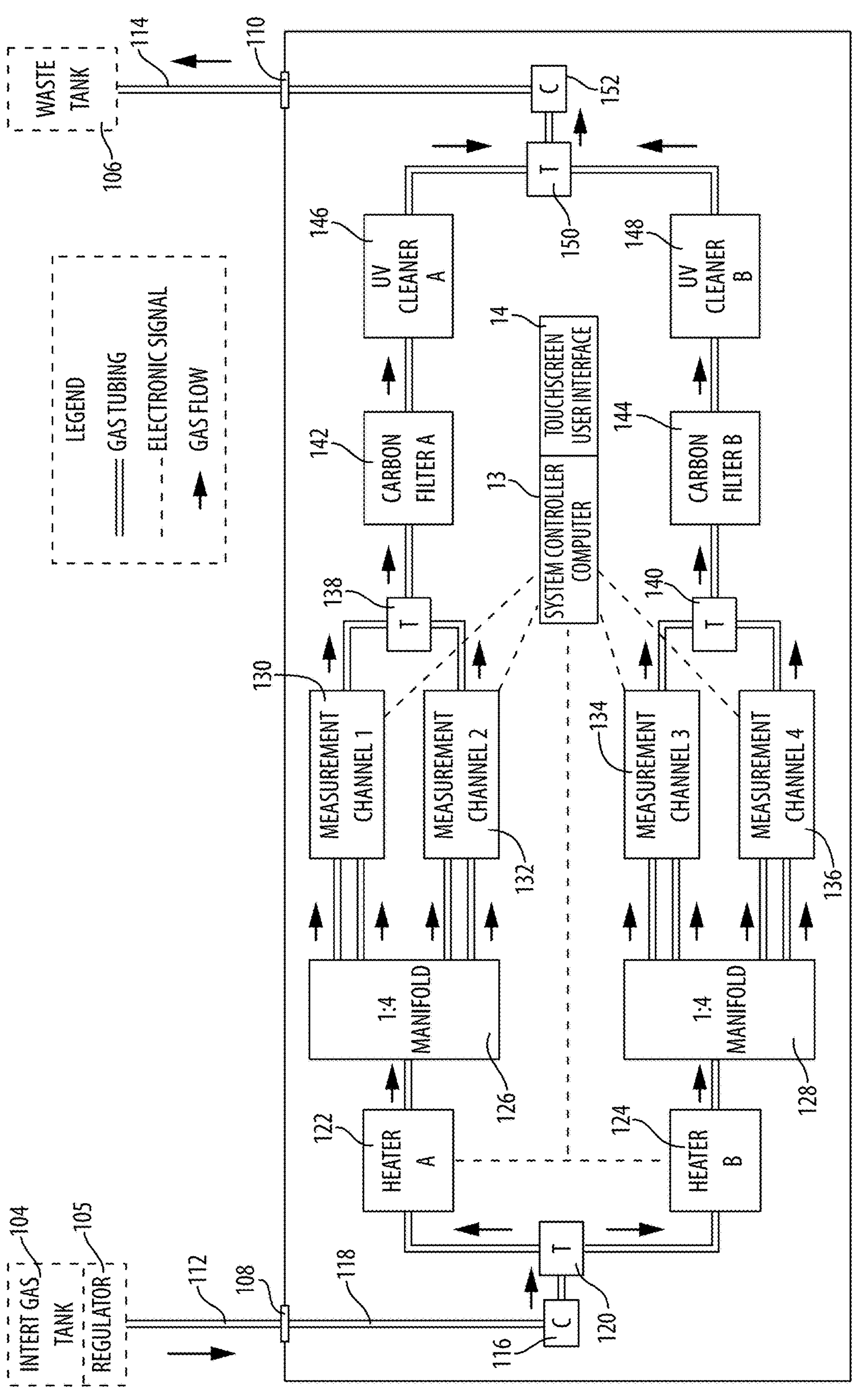
FIG. 2 is a top-level functional block diagram of the apparatus of FIG. 1.

In the preferred embodiment as shown in FIG. 2, four independent but identical VOC measurement channels 130, 132, 134, 136 are implemented. This provides the ability to operate the apparatus 10 in parallel; i.e., with four different specimens (in four different vials 24 as shown in FIG. 22) simultaneously. As indicated above, in the alternative, the apparatus 10 may be operated with a single vial 24 that is tested in each channel sequentially, by testing the specimen in the first measurement channel 130, then rotating the vial block mount so that the same specimen is tested in the second measurement channel 132, etc. through the third and fourth measurement channels 134, 136. This enables various parameters such as heat, VOC concentration, and pressure to be varied if desired with each channel, providing a more robust methodology of testing. Although the preferred embodiment implements four VOC measurement channels, an apparatus may be implemented with any number of channels as may be desired and/or practical.

Describing now the preferred embodiment of four channels as shown in FIG. 2, an inert gas such Argon is supplied by the tank 104 into the apparatus 10 and is fed to two independent gas heaters 122, 124 via input gas tube 118, which connects through a check valve 116 and gas tee 120 to supply the gas heaters 122, 124. Two separate gas heaters 122, 124 are used since the layout of the components in the housing 12 is physically divided into two sides (labelled A & B). In an alternative embodiment, a single heater could be used if desired. Or, if it is desired to heat the gas provided to each channel differently, four separate heaters could be used as well.

Thus, as shown, each side of the housing 12 will contain two independently operating VOC measurement channels (side A includes measurement channels 130, 132; and side B includes measurement channels 134, 136). These four independent VOC measurement channels 130, 132, 134, 136, which operate identically and will be described in further detail with reference to FIG. 3 below.

Referring now to side A, after the incoming gas is (optionally) heated to a desired temperature at heater 122 it is fed through gas tubing to a manifold 126, which will further divide the gas supply into four inputs; two of which are fed into measurement channel 130 and the other two are fed into measurement channel 132. Likewise, on side B, after the incoming gas is (optionally) heated to a desired temperature at heater 124 it is fed through gas tubing to a manifold 128, which will further divide the gas supply into four inputs; two of which are fed into measurement channel 134 and the other two are fed into measurement channel 136.

Figure 3:
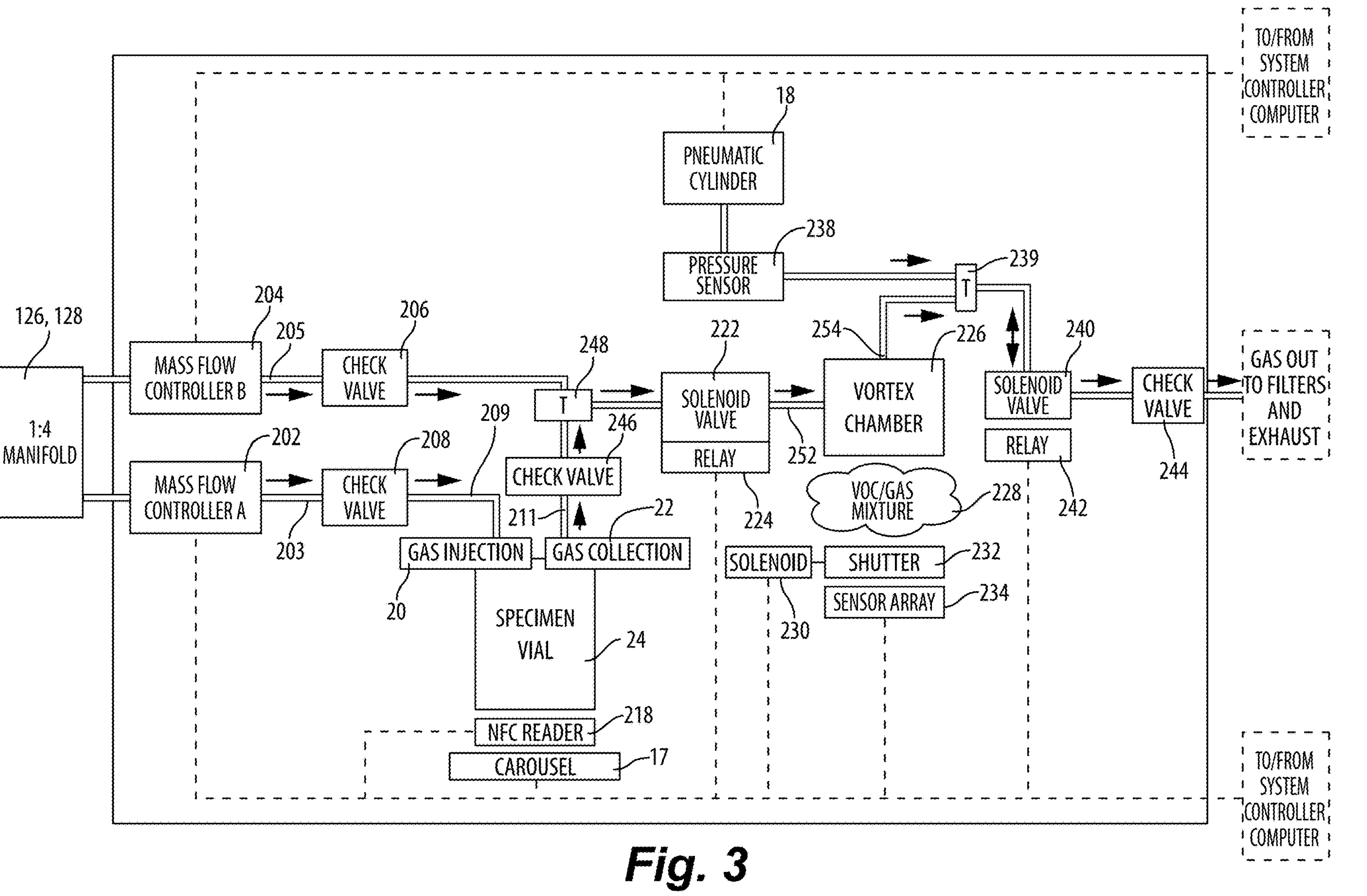
FIG. 3 is a detailed block diagram of each VOC measurement channel implemented in the block diagram of FIG. 2.

Each VOC measurement channel will generate a VOC/gas mixture as will be described in detail below with reference to FIG. 3. The VOC/gas mixtures exit the measurement channels and are mixed together by tees 138, 140, where they are first filtered by a carbon filter 142, 144 and then passed through a UV cleaner 146, 148. These filtered waste gases are again combined at tee 150 and output via the gas valve 110 and exit gas tubing 114 to the waste tank 106 for subsequent storage and disposal.

Check valves 116, 152 are implemented as shown at the gas entry and exit locations to ensure proper direction of the flow of gas.

Also shown in FIG. 2 is the system controller computer 13, which is controlled via the touchscreen user interface 14. The computer 13 is used to control the parameters of operation of the apparatus 10, store locally the results of each VOC measurement, and perform an analysis of each measurement to determine if any disease may be present in any of the specimens, as will be described in detail below.

The VOC measurement channels 130, 132, 134, 136 are now described in detail with reference to FIG. 3. Two of the four gas outputs of the manifold 126 are fed into each VOC measurement channel, one being fed through gas tubing to a mass flow controller A 202 and the other being fed to a mass flow controller B 204.

The mass flow controllers 202, 204 as known in the art are essentially proportionate gas valves that are electronically controlled (manually or by the system controller computer 13) and operate to measure and control the flow of gas from the tank 104 in a more precise manner than is otherwise obtainable with the external regulator 105. In the preferred embodiment, the mass flow controller used is SENSIRION SFC6000-5SLM, although other similar products may also be used.

Thus, the gas flow A 203 output by the mass flow controller A 202 is precisely controlled through the mass flow controller A 202 and fed via a check valve 208 and injection tube 209 to a gas injection device 20. As described below, there are several types of gas injection devices used. In general, the gas injection device is adapted to inject gas from the mass flow controller A 202 into the vial 24 that contains the specimen being tested and causes gas provided from the mass flow controller A 202 to bubble throughout at least a portion of the specimen in the vial 24 such that the gas mixes with volatile organic compounds (VOCs) present in the specimen to create a VOC/gas mixture 228 that is released into the headspace above the specimen in the vial. The gas collection device 22, also described in further detail below, operates to collect the VOC/gas mixture from the headspace in the vial and feed the VOC/gas mixture through collection tube 211 to a first input of a gas mixing tee 248 via the check valve 246.

The other input of the gas mixing tee 248 is fed from the mass flow controller B 204, through the gas flow B 205 through a check valve 206. The mixing tee 248 mixes/combines gas input from the gas collection device 22 with gas received directly from the output of the mass flow controller B 204. The system controller computer 13 is connected to the first mass flow controller A 202 and the second mass flow controller B 204 and is programmed to control a flow rate of the gas through each mass flow controller 202, 204 in order to control the relative concentration of VOCs being supplied from the output of the mixing tee 248. This configuration allows precise control of the amount of gas being fed into the specimen vial 24 (through the gas injection device 20) which results in the VOC/gas mixture fed to the tee 248, as well as the pure gas being fed by the mass flow controller B 204 directly to the tee 248. This allows the system to combine the VOC/gas mixture with pure gas at the tee 248 by controlling the amount(s) of gas through each mass flow controller 202, 204. Thus, the combined gas fed from the output of the tee 248 may be controlled so as to dilute the VOC/gas mixture if desired. Dilution of the VOC/gas mixture may be desired in cases where the VOC/gas mixture is found to be denser than desired, due to various factors in the measurement process. Of course, there could be no dilution if desired by shutting off the mass flow controller 204 as the VOC/gas mixture passes through the tee 248.

The VOC/gas mixture is fed from the mixing tee 248 to solenoid valve 222 and then on to a vortex chamber 226. The solenoid valve 222 is controlled by relay 224 so that the flow of the VOC/gas mixture may be prevented from entering the vortex chamber 226 when desired and allowed to enter the vortex chamber by operating the relay 224.

Figure 27:
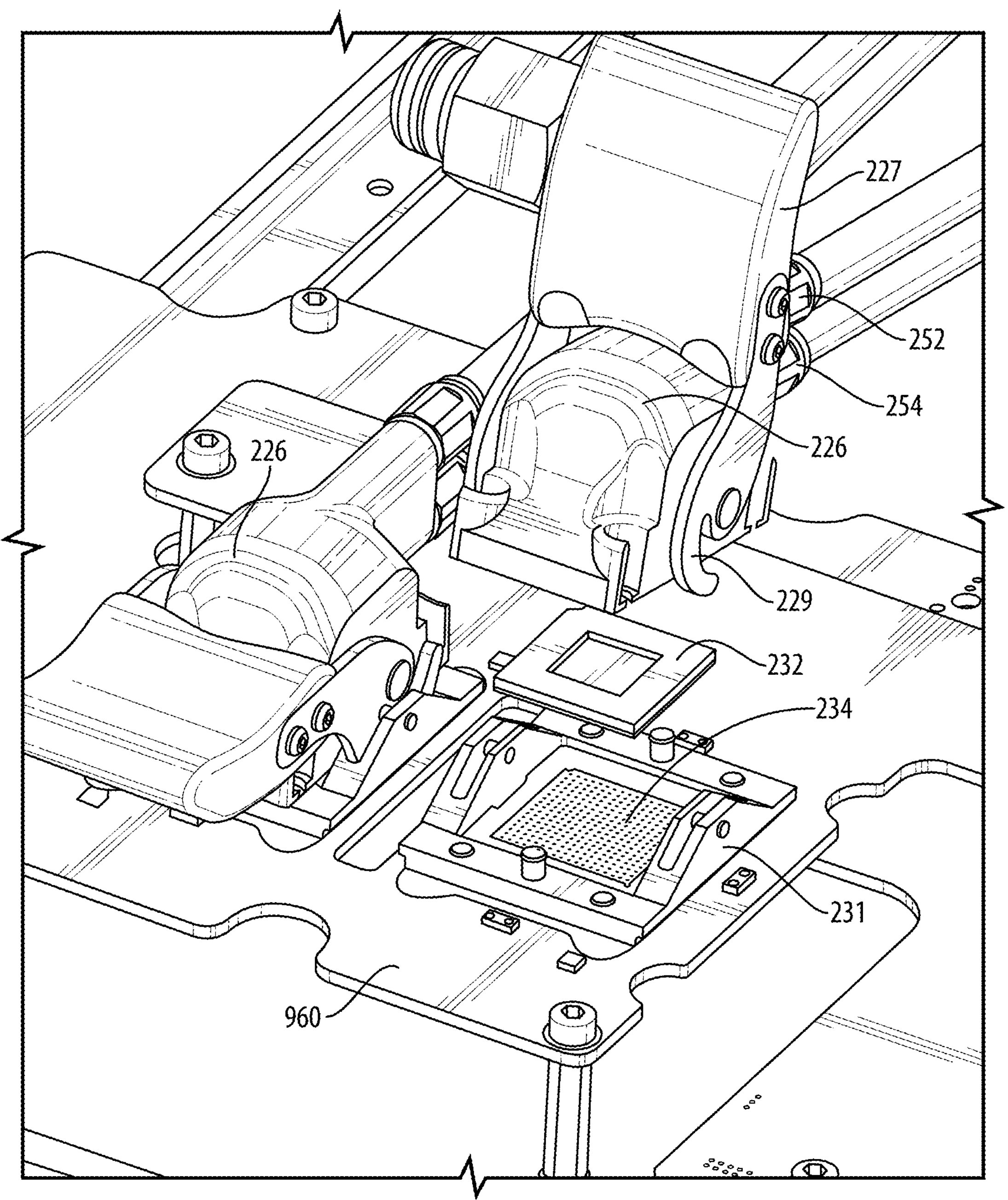
FIG. 27 illustrates a PC board assembly that houses the vortex chambers.

The vortex chamber 226, as shown in FIG. 27, is essentially a dome-shaped chamber into which the VOC/gas mixture 228 is fed and passed over a sensor array 234 that is located in proximity to (within or next to) the vortex chamber 226 and attached to the sensor PC board 960. In the preferred embodiment, there are two sensor arrays 234 located on each of two sensor PC boards 960 for a total of four sensor arrays 234 (i.e., one for each measurement channel). The sensor array 234 in the preferred embodiment has 256 channels (individual sensors), but the number of channels may be varied as desired. Each individual sensor is coated with DNA on top of an array of carbon nanotubes and is capable of measuring minute changes in electrical impulses caused by the presence of certain VOCs through impedance changes. Each sensor contains a single strand of DNA (16 different types of DNA are used in the preferred embodiment). Certain strands of DNA will attract certain types of molecules more than others; therefore, by selecting the desired DNA, the desired VOCs may be collected and measured accordingly. As the VOC data is collected, it is analyzed in real time or offline by the system controller computer 13 with respect to known patterns and signatures (for example through artificial intelligence and/or machine learning algorithms), so that known diseases will be detected by matching of preexisting patterns. In the alternative, the pattern matching process could be executed by an external computer rather than or in addition to the internal computer 13.

Implementation of a sensor array to detect the presence of VOCs in a gas is explained further in, for example, Johnson et al., U.S. Pat. No. 11,415,546, VOLATILE ORGANIC COMPOUND-BASED DIAGNOSTIC SYSTEMS AND METHODS, Aug. 16, 2022, which is incorporated by reference herein. See also Postrel, U.S. Pat. No. 12,031,935, INSTANT EARLY STAGE DISEASE DETECTION BY DECODING ORGANIC COMPOUND SIGNATURES, Jul. 9, 2024, which is incorporated by reference herein.

The vortex generator 226 will circulate the VOC/gas mixture 228 so that the sensor array 234 can better detect the presence of the VOCs from the mixture. Each vortex chamber 226 has a chamber intake port 252 and a chamber exhaust port 254 to allow free flow of the VOC/gas mixture 228 (flexible tubing that supplies the gas mixture omitted for clarity).

The flow of the VOC/gas mixture 228 is controllable within and through the vortex chamber 226 as desired. The solenoid valve 222 is located near the intake port 252 as described and is under automatic control of the system controller computer 13 and/or manual control by an operator. By selectively opening and closing the solenoid valve 222, flow of the VOC/gas mixture 228 into the chamber 226 is controlled.

The vortex chamber 226 is a passive device, such that the VOC/gas mixture 228 is introduced into the chamber, where it swirls around and then exits after being passed over the sensor array 234. In an alternative embodiment, a powered turbine may be used to circulate the VOC/gas mixture 228 near the sensor array 234. The turbine uses a magnetically levitated impeller that swirls the VOC/gas mixture 228 and pushes the mixture down to the sensor array 234 for detection.

An optional shutter 232 is located in the vortex chamber 226 in order to control, via a shutter solenoid 230, the presence of the VOC/gas mixture over the sensor array 234 as desired. That is, by closing the shutter 232, the VOC/gas mixture in the chamber is blocked from the sensor array 234, and opening the shutter 232 enables the sensor array 234 to access the VOC/gas mixture when desired.

Each channel of the apparatus 10 also has a pneumatic cylinder 18 coupled via a pressure sensor 238 and tee 239 to the exit port of the chamber 226 as shown. The pneumatic cylinder 18 is operated in conjunction with solenoid valve 240 and relay 242 to control pressure within the chamber 226 and thus to control the flow of the VOC/gas mixture 228 through the chamber. For example, the output valve 240 could be closed completely, this forcing recirculation of the gas mixture 228 over the sensor array. An example of a pneumatic cylinder used in this embodiment is one available from AIRPOT, Piston Cylinder 122468-1.

Thus, by selectively controlling the mass flow controllers 202, 204, the solenoid valve 222 at the input of the vortex chamber 226, the pneumatic cylinder 18, the shutter 232, and the solenoid valve 240, the operator may either manually (or by computer control) control gas flow rate, VOC concentration, pressurization in the chamber, and duration of exposure to the sensor array of the VOC/gas mixture, thereby controlling many aspects of the measurements taken as needed.

After the VOC/gas mixture 228 has passed over the sensor array 234, it passes through check valve 244 to be mixed at the tee 138, 140 (see FIG. 2) to the carbon filter 142, 144 and UV cleaner 146, 148. From there, the filtered gas mixture exits the housing 12 through the output gas valve 110 and the exit gas tubing 114 to the external waste tank 106.

Figure 4:
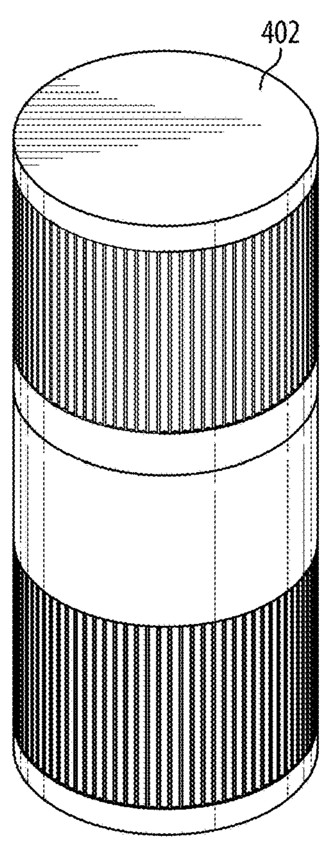
FIG. 4 is a perspective view of a specimen vial container used to safely hold the vial for transport.

FIG. 4 is a perspective view of a specimen vial carrier 402 used to safely hold the vial 24 for transport from the site of collection (e.g. a doctor's office) to the testing site. FIG. 5 is an exploded view of the specimen vial 24 and its carrier 402. The vial 24 will be placed within the lower basket 410, which is lowered into the carrier base 406. A mating upper basket 408 is then placed over the top of the vial 24, and finally the carrier top 404 is placed over the assembly and threaded onto the carrier base 406 to secure the vial 24 within. The upper basket 408 and lower basket 410 will keep the vial isolated and will function as shock absorbers to help prevent the vial from breaking in transit. All components of the vial carrier 402 are preferably fabricated from a plastic material.

The various gas injection devices 20 that inject the inert gas supplied by the external gas tank 104 and inject the gas into the specimen in the vial 24 to create the VOC/gas mixture in the vial headspace, as well as the accompanying gas collection devices 22 that collect the VOC/gas mixture from the headspace in the vial and supply it to the vortex chamber 226 for processing by the sensor array 234, will now be described in detail.

Figures 6, 7:
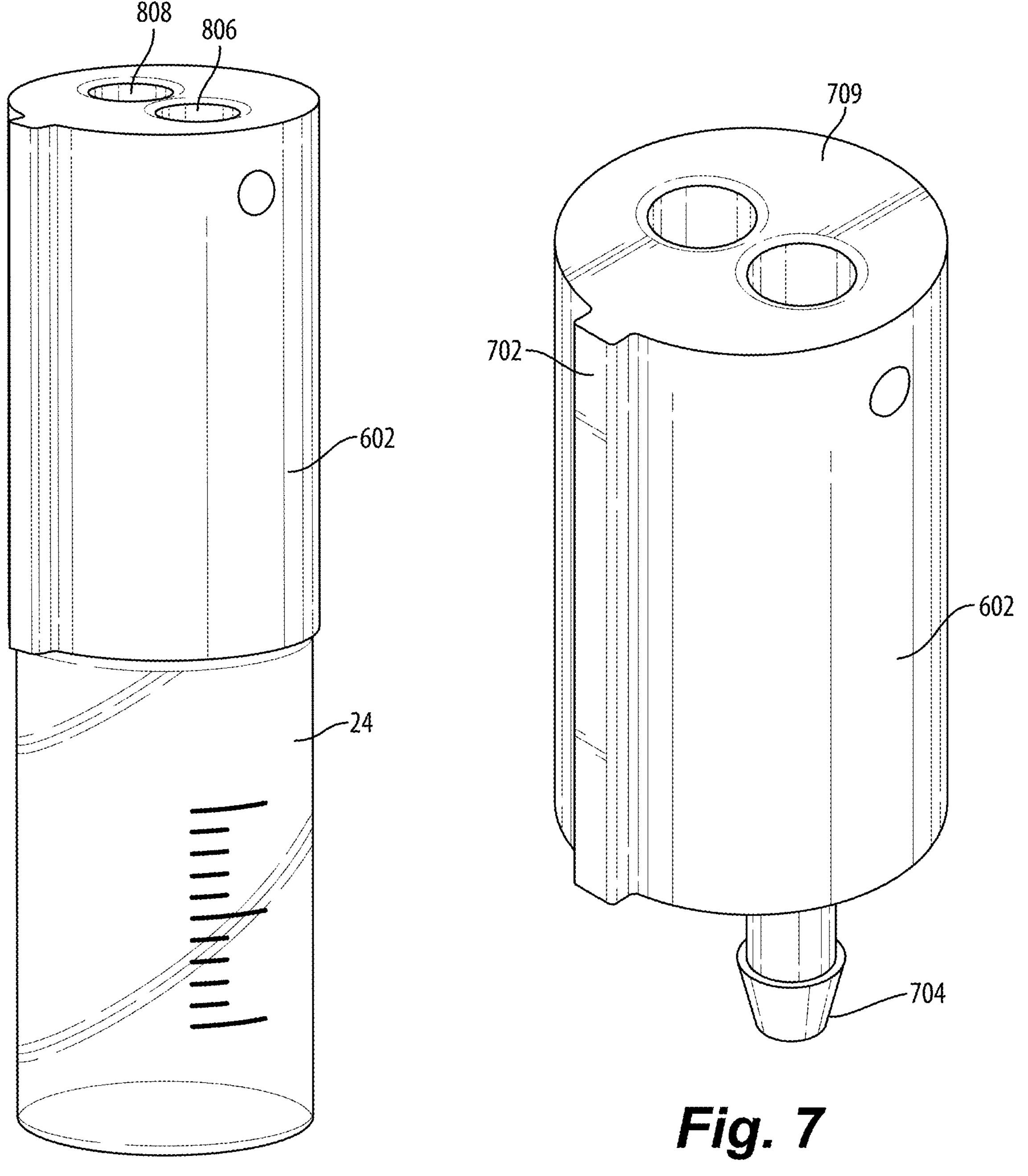
FIG. 6 is an illustration of a specimen vial and vial cap with a gas injection device and gas collection device in a first embodiment.
FIG. 7 is a top perspective view of the vial cap of FIG. 6.
Figure 8:
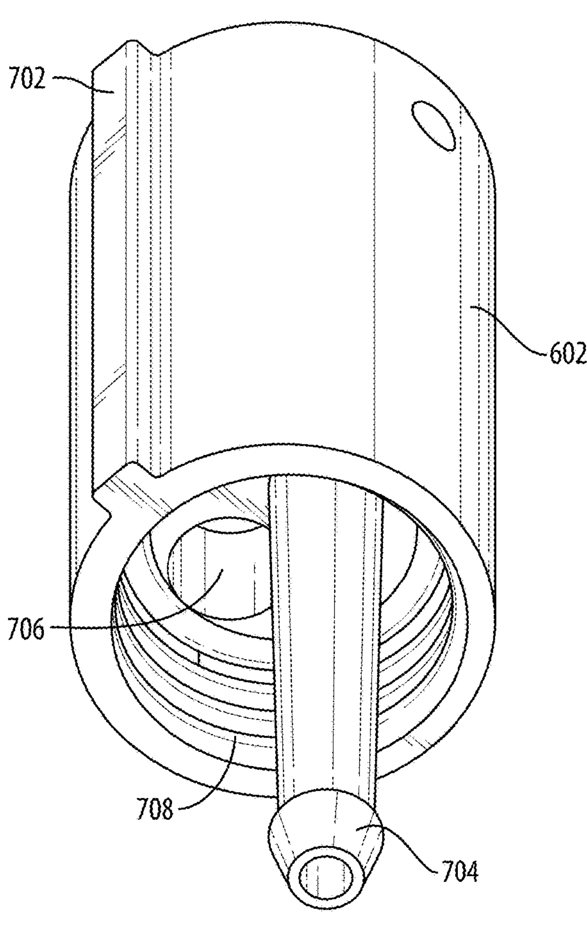
FIG. 8 is a bottom perspective view of the vial cap of FIG. 6.
Figure 9:
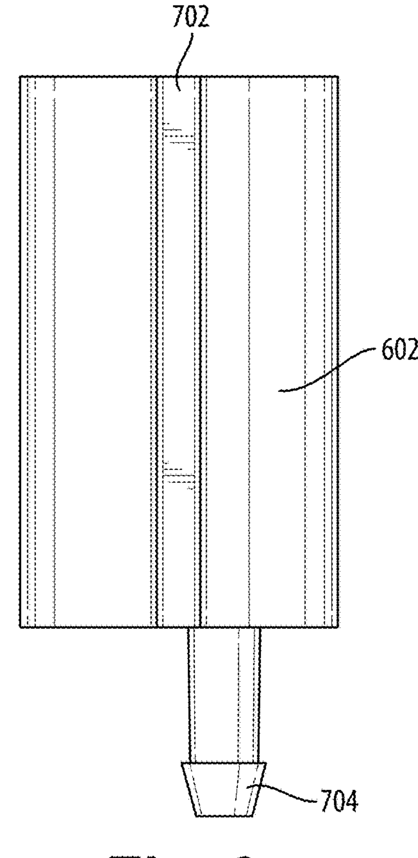
FIG. 9 is a side view of the vial cap of FIG. 6.
Figure 12:
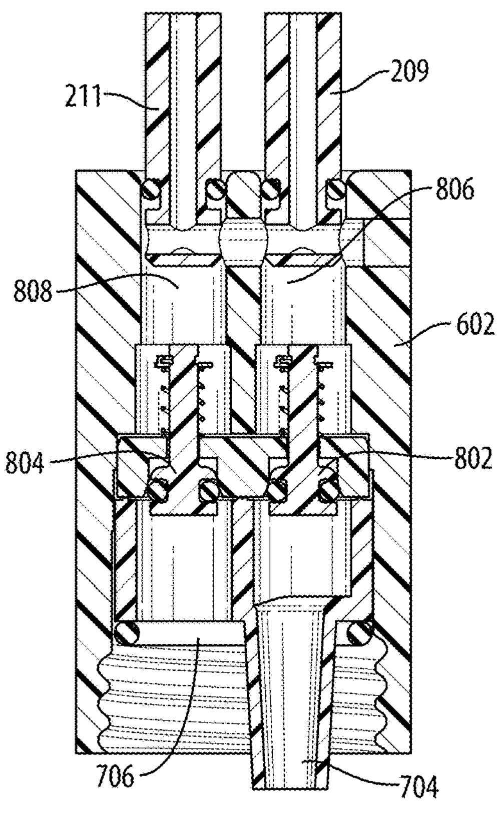
FIG. 12 is a cross-section view of the vial cap of FIG. 6 with an injection tube and collection tube inserted but not fully engaged with the valves.
Figure 13:
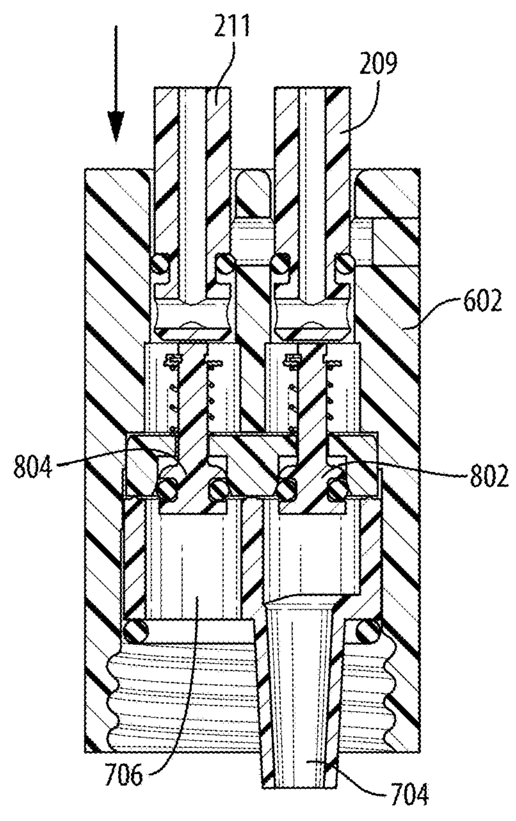
FIG. 13 is a cross-section view of the vial cap of FIG. 6 with an injection tube and collection tube making initial contact with the valves.
Figure 14:
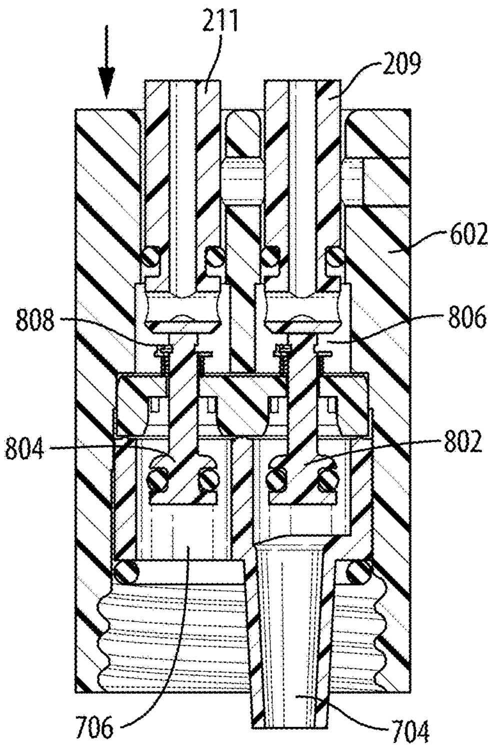
FIG. 14 is a cross-section view of the vial cap of FIG. 6 with an injection tube and collection tube fully pressed against the valves to seal against the upper part of the vial cap, pressurizing the system.

FIGS. 6-11 illustrate a specimen vial 24 and vial cap 602 with a gas injection device and gas collection device in a first embodiment, referred to as the valved embodiment, and FIGS. 12-14 illustrate the operation of this first embodiment. The vial 24 is shown in FIG. 6 with a valved cap 602 inserted thereon. As previously described, the generic cap 25 will be removed from the vial at the testing site, and in this case replaced by the technician with the valved cap 602 using threads 708. The valved cap 602 is also provided with an O-ring 707 to ensure a snug fit and no loss of gas pressurization during operation.

Figure 24:
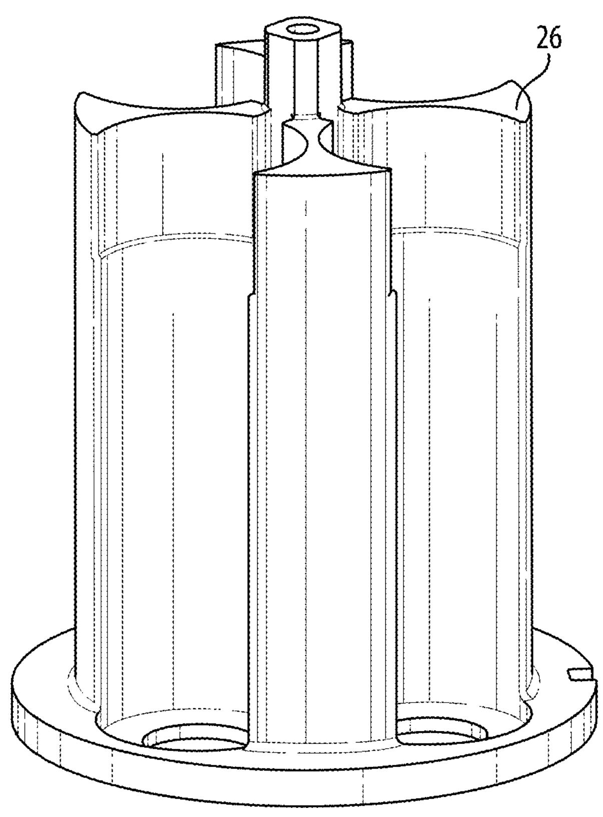
FIG. 24 is an illustration of the vial block of FIG. 22.

The valved cap 602 has an index 702 which is used for registration with the vial block 26 (see FIG. 24). This ensures that the cap 602 will be located at a specific position to enable the injection tube 209 and collection tube 211 to be precisely and accurately lowered into and inserted within the mating gas input passageway 806 and gas output passageway 808, respectively (see FIG. 12). As shown in FIG. 3, the injection tube 209 provides gas flow from the mass flow controller A 202 (via check valve 208) directly to the gas injection device 20, which in this valved embodiment includes the gas input passageway 806. Likewise, the collection tube 211 provides gas flow from the gas collection device 22, which in this valved embodiment includes the gas output passageway 808, directly to the mixing tee 248 (via check valve 246).

Figure 10:
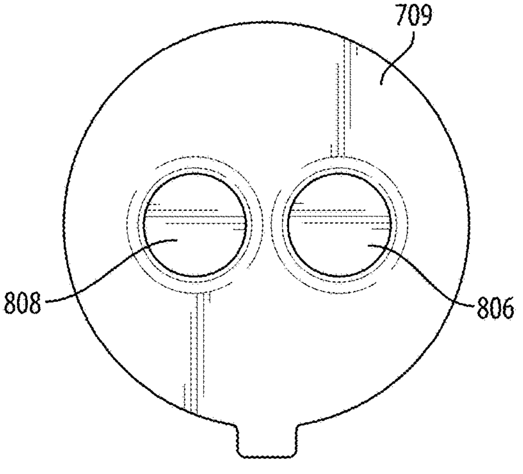
FIG. 10 is a top view of the vial cap of FIG. 6.
Figure 11:
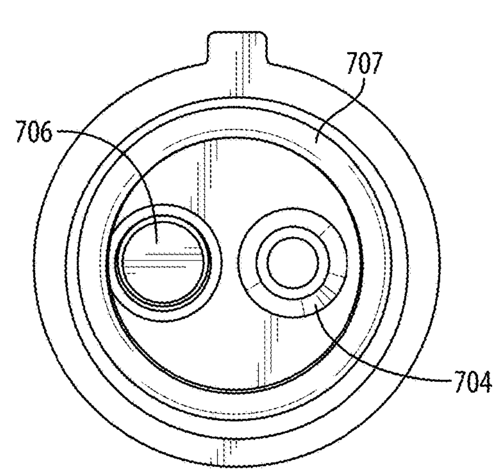
FIG. 11 is a bottom view of the vial cap of FIG. 6.

As also shown by the top view of FIG. 10, the top surface 709 of the valved cap 602 provides the gas input passageway 806 and gas output passageway 808. As shown in FIG. 12, the gas input passageway leads to the first side of a gas injection valve 802. There is also shown an injection passageway 704 coupled to the second side of the gas injection valve 802. When the injection tube 209 is inserted into the gas input passageway 806 and makes contact with and is urged against the first side of the gas injection valve 802 as shown in FIGS. 13 and 14, the gas injection valve 802 is caused to open and the gas may be injected into the specimen in the vial via the open gas injection valve 802 and into the injection passageway 704.

The injection passageway 704 has at least one injection passageway opening at the tip thereof that extends below the headspace and into the specimen in the vial. Optionally, the injection passageway 704 may have a multiplicity of injection passageway openings located throughout a portion of the injection passageway 704 that extends into the specimen, such that the inert gas injected via the open gas injection valve 802 passes through the multiplicity of injection passageway openings into the specimen, causing a micro-bubbling of the inert gas within the specimen that results in the VOC/gas mixture. The injection passageway may also include a diffusion stone (not shown) that extends into the specimen, such that the injected gas passes through the diffusion stone into the specimen, causing a micro-bubbling of the inert gas within the specimen that results in the VOC/gas mixture in the headspace.

In this first (valved) embodiment, the gas collection device 22 includes a gas output passageway 808 in the valved cap 602, which is coupled to the first side of a gas collection valve 804 in the cap 602. A collection passageway 706 in the vial cap is coupled to the second side of the gas collection valve 804, the collection passageway adjoining the headspace but not extending into the specimen. The collection tube 211 is coupled to the first input of the mixing tee 248. When the collection tube 211 is inserted into the gas output passageway 808 and makes contact with and is urged against the first side of the gas collection valve 804 as shown in FIGS. 13 and 14, the gas collection valve 804 is caused to open and the VOC/gas mixture is collected from the headspace via the open gas collection valve and into the gas output passageway 808 and to the collection tube 211 to be supplied to the mixing tee 248.

Figures 15, 16:
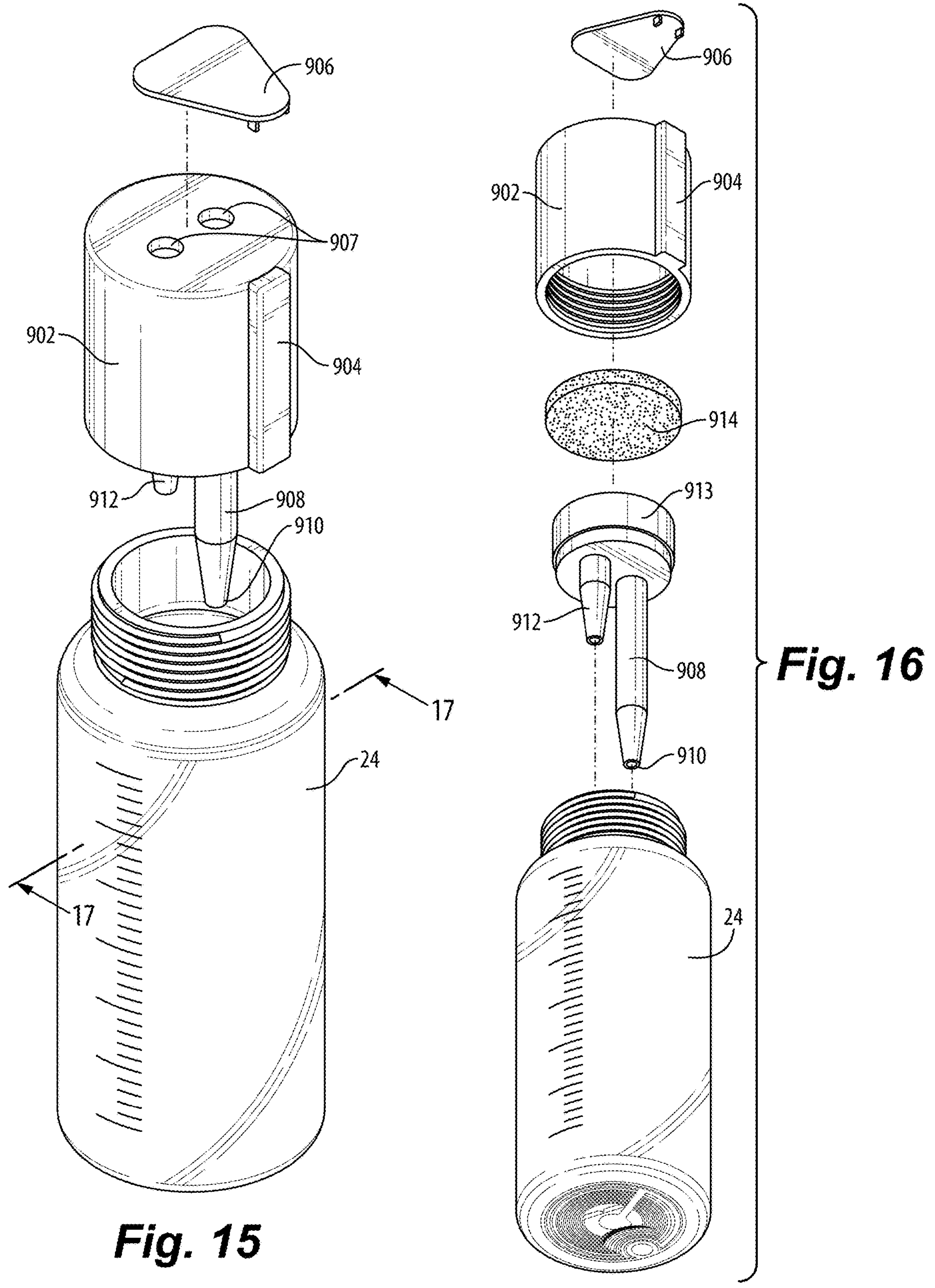
FIG. 15 is a first exploded view of a specimen vial and vial cap with a gas injection device and gas collection device in a second embodiment.
FIG. 16 is a more detailed exploded view of the specimen vial and vial cap of FIG. 15.
Figures 17, 18:
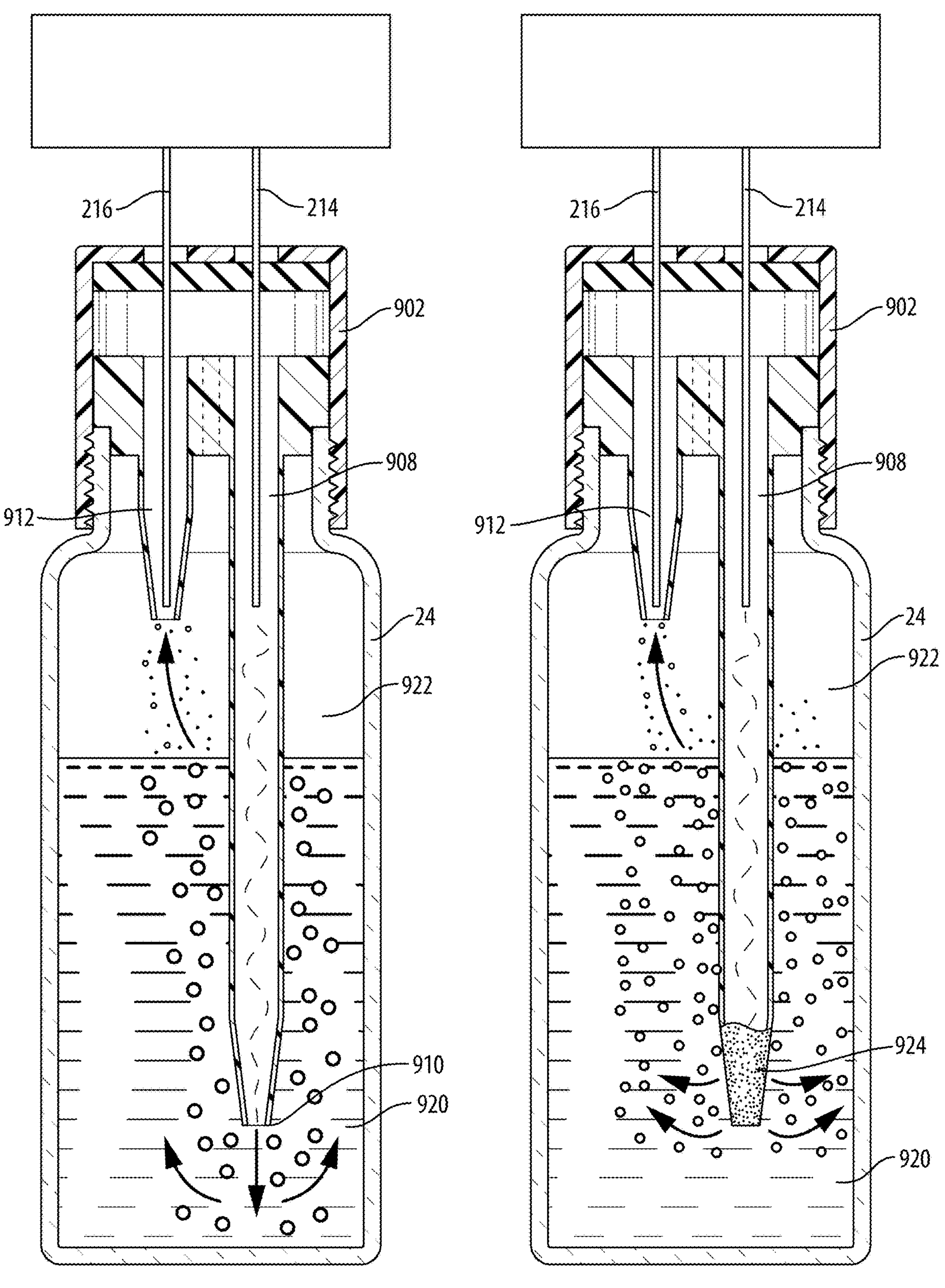
FIG. 17 is a cross-section view of the specimen vial and vial cap of FIG. 15 with an injection needle and collection needle inserted through the cap membrane showing gas bubbling through a single injection passageway opening at the end of the injection passageway.
FIG. 18 is a cross-section view an alternative configuration of the specimen vial and vial cap of FIG. 15 with an injection needle and collection needle inserted through the cap membrane showing gas bubbling through a multiplicity of injection passageway openings.

FIGS. 15-16 illustrate a specimen vial and vial cap with a gas injection device and gas collection device in a second embodiment, referred to as the needle/passageway embodiment, and FIGS. 17-18 illustrate the operation of this second embodiment. The vial 24 is shown in FIG. 15 with a vial cap 902 inserted thereon. As previously described, the generic cap 25 will be removed from the vial at the testing site, and in this case replaced by the technician with the cap 902. The cap 902 is also provided with an O-ring (not shown) to ensure a snug fit and no loss of gas pressurization during operation.

In this second embodiment, rather than utilizing the injection tube 209 to supply gas directly to the specimen in the vial and the collection tube 211 to collect the VOC/gas mixture directly from the headspace as in the first embodiment, a pair of hypodermic needles (injection needle 214 and collection needle 216) are coupled to tubes 209, 211 and used to perform these functions as will be described.

The cap 902 is provided with a disk 913 that encompasses an injection passageway 908 and collection passageway 912 extending therefrom, as shown in FIG. 16. Also shown is a membrane 914 located just above the disk 913. The cap 902 has a pair of apertures 907 in alignment with the injection passageway 908 and collection passageway 912, the apertures being large enough to allow the injection needle 214 and collection needle 216 to pass through. A cover 906 is provided to protect the membrane when the vial is not in use.

The membrane 914 may be a thick piece of silicone with a thinner layer of polytetrafluoroethylene (PTFE, such as TEFLON). The PTFE layer will prevent out-gassing into or out of the vial 24. The silicone/PTFE layer allows repeated insertion and removal of the injection needle 214 and the collection needle 216 without coring the membrane.

As with the first embodiment, the cap 902 has an index 904 which is used for registration with the vial block 26 (see FIG. 24). This ensures that the cap 902 will be located at a specific position to enable the needles 214, 216 to align with the apertures 907, the injection passageway 908, and the collection passageway 912. Instead of two apertures 907, a single larger aperture may be used in their place.

As shown in FIG. 17, at the distal end of the injection passageway 908 is at least one injection passageway opening 910, which will extend below the headspace 922 and into the specimen 920. In this case, the injection needle 214 is inserted through the membrane 914 such that the tip of the injection needle 214 extends into the injection passageway 908, but not into the specimen 920 directly. When the gas is supplied from the mass controller A 202 to the injection needle 214, it is injected into the specimen 920 via the injection passageway opening 910, causing percolation of the gas with the specimen to create the VOC/gas mixture in the headspace 922.

In an alternative embodiment, as shown in FIG. 18, the injection passageway 908 has a multiplicity of injection passageway openings 924 located throughout a portion of the injection passageway 908 that extends into the specimen, such that the gas injected via the injection needle 214 passes through the multiplicity of injection passageway openings 924 into the specimen, causing a micro-bubbling of the gas within the specimen that results in the VOC/gas mixture in the headspace. Further optionally, the injection passageway 908 has a diffusion stone (not shown) that extends into the specimen, such that the gas injected via the injection needle 214 passes through the diffusion stone into the specimen, causing a micro-bubbling of the inert gas within the specimen that results in the VOC/gas mixture.

The gas collection device 22 in this embodiment similarly has a collection passageway 912 as shown in FIGS. 15-18. At the distal end of the collection passageway 912 is at least one opening which will extend only into the headspace 922 and not into the specimen 920. The gas collection device includes the collection needle 216 inserted through the membrane 914 such that the tip of the collection needle extends into the collection passageway, such that the VOC/gas mixture is collected from the headspace via the tip of the collection needle 216 and supplied to the mixing tee 248.

Figure 19:
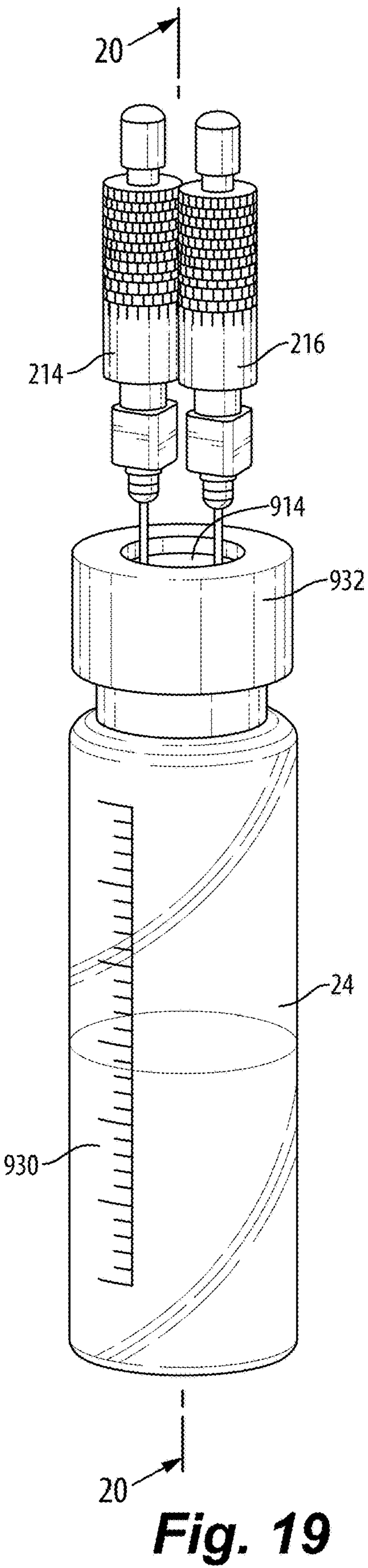
FIG. 19 is a perspective view of a specimen vial and vial cap with a gas injection device and gas collection device in a third embodiment.
Figure 20:
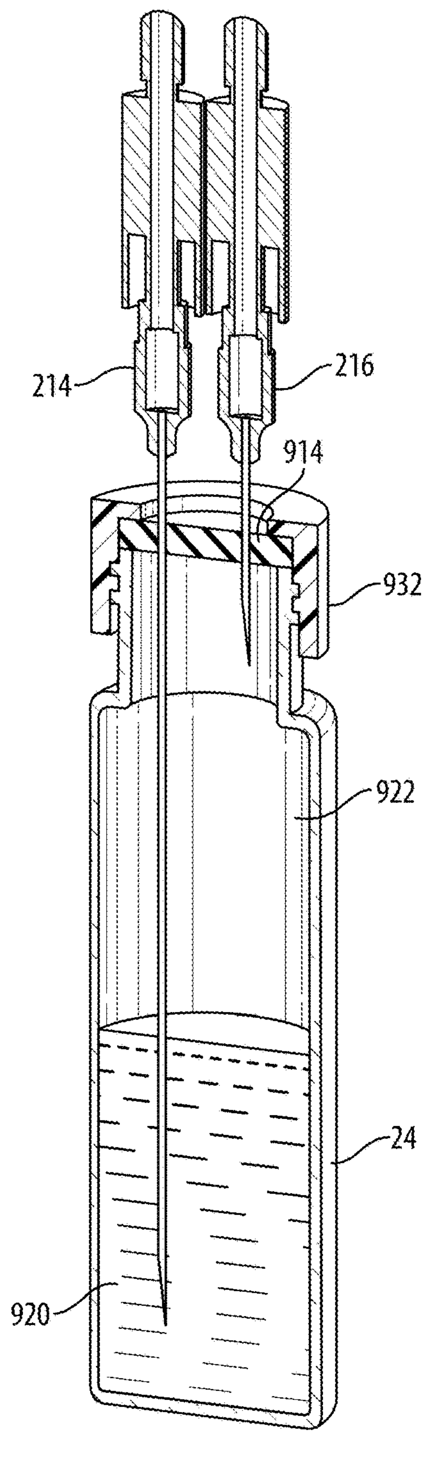
FIG. 20 is a cross-section view of the specimen vial and vial cap with a gas injection device and gas collection device of FIG. 19.

In a third embodiment shown in FIGS. 19-20, the gas injection device is similar to that of the second embodiment above in that it utilizes an injection needle 214 and a collection needle 216 to pass through a membrane 914 in the cap 932, but the injection passageway 908 and collection passageway 912 are omitted. In this case, the injection needle 214 is inserted through the membrane 914 such that its tip extends below the headspace and directly into the specimen, and the gas is injected directly into the specimen via the tip of the injection needle 214. Similarly, the collection needle 216 is inserted through the membrane 914 such that its tip extends into the headspace but not into the specimen, such that the VOC/gas mixture is collected from the headspace via the tip of the collection needle. As can be seen from FIG. 20, the injection needle 214 is long enough for its tip to be inserted into the specimen 920 being analyzed, while the collection needle 216 is short enough for its tip to be located within the headspace 922 above the specimen 920 for VOC/gas mixture collection purposes.

The injection needle 214 is lowered into the vial 24 so that the membrane 914 is penetrated and the tip of the injection needle 214 is submerged below the headspace 922 and directly into the specimen 920. In this embodiment, the gas supplied via the mass flow controller A 202 is injected through the injection tube 209 directly into the specimen 920 via the tip of the injection needle 214.

Similarly, the gas collection device 22 collects the VOC/gas mixture from the headspace 922 in the vial 24 and feeds the VOC/gas mixture through the collection tube 211 to the first input of the mixing tee 248. In this embodiment, the gas collection device 22 has a collection needle 216 that has been lowered into the vial 24 so that the membrane 914 is penetrated and the tip of the collection needle 216 is submerged into only the headspace and not into the specimen. In this embodiment, the VOC/gas mixture 228 that has percolated from the specimen is collected from the headspace via the tip of the collection needle 216 and sent to the mixing tee 248.

For the second and third embodiments of the gas injection device 20 and gas collection device 22 that utilize the injection needle 214 and collection needle 216, vials 24 that are ready for specimen collection are provided (without needles 214, 216) to the specimen sample collection site (e.g. hospital, clinic, doctor's office etc.), and the health care provider may collect the specimen sample as follows. The patient will urinate into a cup as known in the prior art, and the health care provider will extract the desired amount of the urine using a separately provided disposable hypodermic needle, inject the urine sample into the vial 24 (through the membrane 914), and scan a bar code on the side of the vial 24 and/or NFC chip 940 for identification, wherein the bar code and NFC chip are linked to the patient for anonymous record keeping purposes. This disposable hypodermic needle is provided with a non-coring tip so that the membrane 914 is not cored or otherwise compromised during insertion of the needle and injection of the sample. The vial 24 may then be provided to the testing laboratory where the apparatus of the present invention will be operated to analyze the VOCs of the specimen provided. The testing apparatus may also be located at the site of the specimen collection e.g., the hospital or clinic. On arrival at the testing facility, the bar code on the vial is scanned and optionally linked to data in the NFC chip for identification purposes, again on an anonymous basis. This will maintain the chain of custody of the vial/sample without violating the privacy of the patient.

Figure 21:
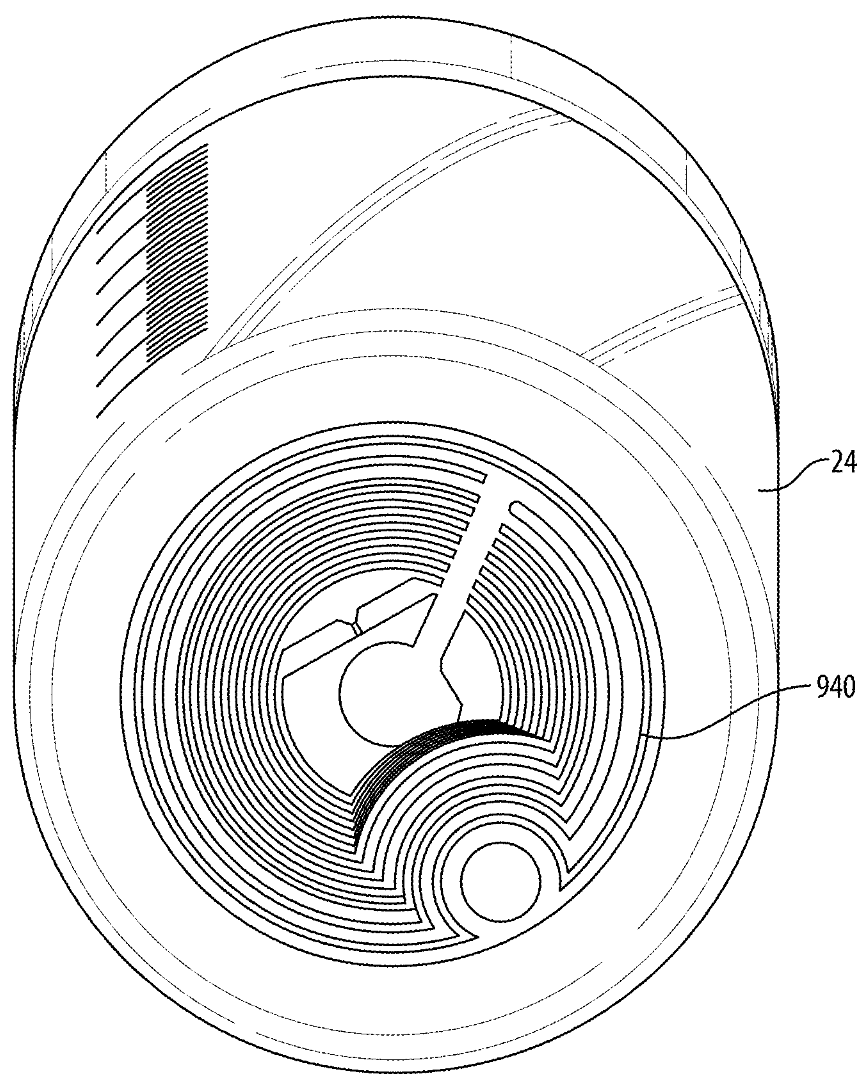
FIG. 21 is an illustration of a near field communication (NFC) antenna and chip assembly on the bottom of the vial.
Figure 25:
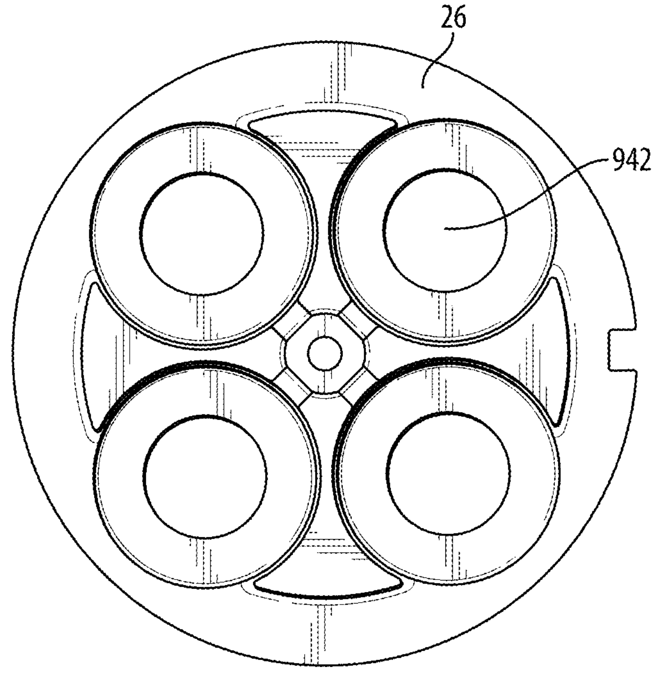
FIG. 25 is a top plan view of the vial block of FIG. 22.

FIG. 21 is an illustration of a near field communication (NFC) antenna and chip assembly 940 having 180 bytes of read/write memory located on the bottom of the vial 24, which can be written to and read from by an NFC reader 218 (see FIG. 3) for tracking and other identification purposes. The NFC reader 218 may be located below one of the apertures 942 of the vial block 26 as shown in FIGS. 24 and 25 to enable access by the reader 218 to the NFC chip 940 of the vial 24 placed over that aperture in the vial block. A bar code (not shown) may optionally be located on the vial 24 that also may be used for identification purposes. The bar code may be a linear one-dimensional bar code or a more densely packed two-dimensional bar code such as a QR code, as desired.

The vial 24 may be partially filled with an inert gas such as Argon prior to being provided to the health care professional that will be obtaining the patient's specimen (or it may simply be empty). In the case where inert gas is used, a volume of the interior space that is intended to be filled with the patient's specimen is left in a vacuum so that the specimen sample is easily injected into the vial. That is, the pressure of the Argon gas in the vial 24 is less than atmospheric, so that when the urine sample is injected into the vial, the pressure inside is equalized with the pressure outside the vial. Optionally an anti-bacterial ingredient may be added to the vial 24 in the event that the sample being deposited is contaminated.

Injection needles 214 and collection needles 216 are intended to be reusable, rather than the disposable needles used at the sample collection site to inject the sample into the sealed vial 24. Needles 214, 216 are precision made, having for example stainless steel components rather than plastic. The tips of the needles 214, 216 have a geometry that will prevent the 3 mm silicon membrane from being cored as they are inserted therethrough. That is, a typically non-coring tip will cut through the membrane on insertion and grab a portion of the membrane which gets stuck inside the needle. The non-coring tip will prevent that from happening.

Although the non-coring needles 214, 216 are intended to be reused, they will be changed out periodically in order to prevent problems from occurring. A force sensor may be implemented in order to measure the force needed to insert the needles through the membrane at any given time. If the required force exceeds a predetermined threshold, then a failure is indicated and the needles 214, 216 will be replaced, as further described below.

As explained above, this invention contemplates the implementation of multiple VOC measurement channels as were just described. With reference again to FIG. 2, a four-channel embodiment is shown, in which a rotating vial block mount 16 as shown in FIGS. 1 and 22 is provided in the apparatus, which is used to hold the four vials 24 of specimens within the vial block 26. In one embodiment, four vials 24 containing four different specimens may be inserted into the vial block 26, and the four independent measurement channels are then used to extract the VOCs and generate four separate electrical signals, one for each vial placed in the vial block 26. In this embodiment, specimens may be processed in parallel, at approximately four times the speed of a single vial in a single measurement channel.

In another embodiment, a single vial 24 may be placed in the vial block 26, which may be rotated around to be sampled by each of the four channels in succession. In this manner, four times as much data is obtained for a single specimen than would otherwise be available with only a single channel.

FIG. 22 is a closeup view of a vial block mount 16 and vial block 26 containing four specimen vials 24. NFC reader 218 is located underneath the vial block mount 16 and is positioned to read the NFC chip 940 from each vial 24 as the vial block mount 16 is rotated from each position by the motorized carousel 17 located underneath the vial block mount 16. The operation of the vial block mount 16 is controlled manually or automatically via the system controller computer 13.

FIG. 23 is an illustration of an optional flexible polyimide heating strip 950, which may be located around the rim of the vial block mount 16 as shown in FIG. 22. An example of such a heating strip is an OMEGA KHLV-0504 or KHLV-0502. When implemented, the heating strip is activated and heat will transfer to the vial block mount and vial block, both of which are aluminum, through radiation heating. Heat then transfers from the vial block to each vial and from the vial block mount to the vial block through conduction. Control of the heating strip may be implemented with a thermocouple controlled by the system computer, if desired.

Figure 26:
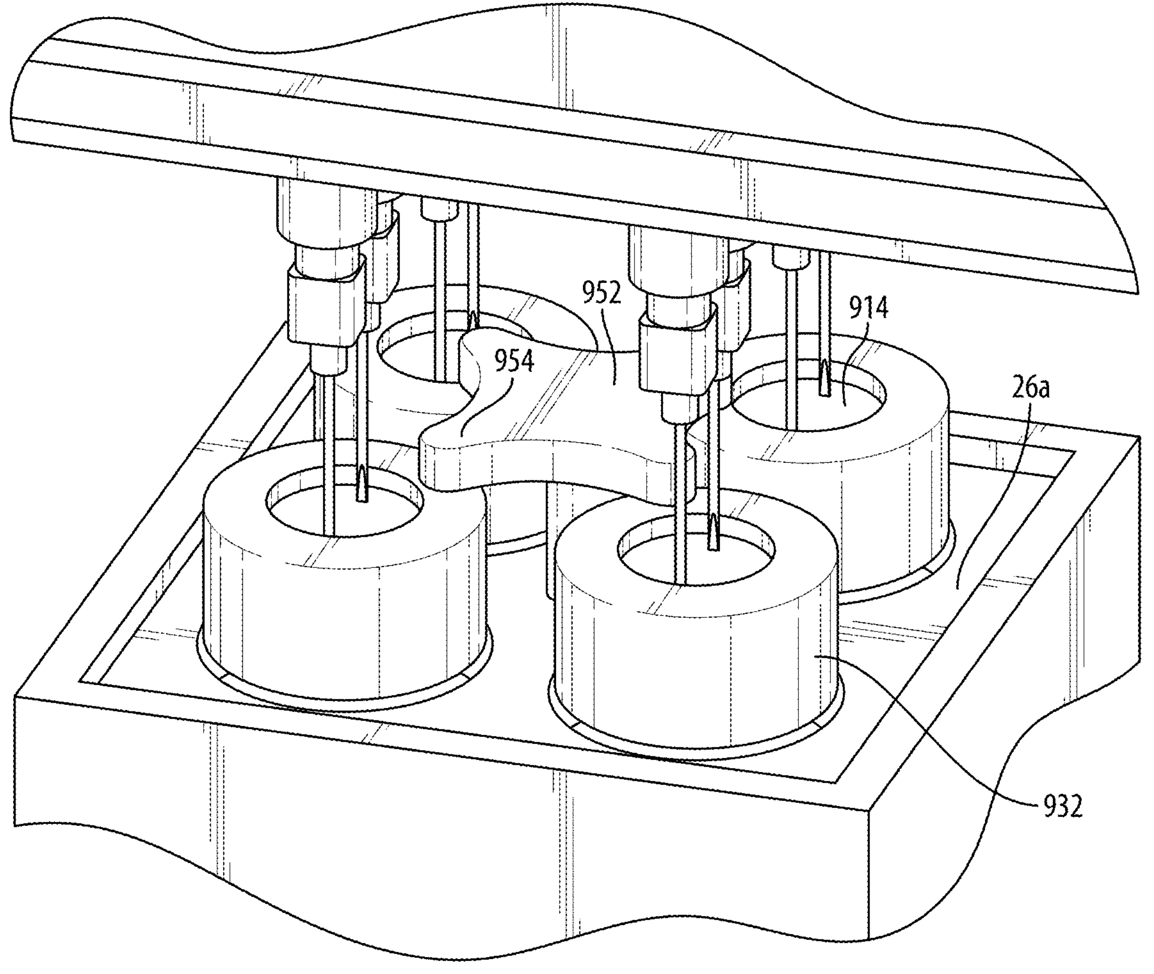
FIG. 26 illustrates a locking mechanism for securing the vials in an alternative shaped vial block.

FIG. 23 also shows a locking mechanism 952, shown in more detail in FIG. 26. FIG. 26 is an illustration of four vials being tested simultaneously by four sets of injection and collection needles, which may be applicable to either of the gas injection and gas collection device embodiments described above (i.e., needle-only or needles with injection and collection passageways within the vials). Note that the vial block 26*a* shown in FIG. 26 is an alternative cube format; the locking mechanism 952 is applicable to the cylindrical vial block 26 as well.

Here, there are four pairs of injection and collection needles 214, 216, each pair utilized with a separate measurement channel. The locking mechanism 952 may be used to enable the vials 24 to be held in place within the vial block 26, 26*a* while the needles 214, 216 are being withdrawn from the vials, since the vials would otherwise tend to raise with the needles as they are extracted from the membranes 914. By turning the locking mechanism 952 in either direction, the arms 954 will rotate into the empty space between the vials 24 and allow the operator to remove or insert vials when desired. The locking mechanism 952 may be controlled by a motor (not shown) and controlled by the operator via the touchscreen interface 14, or it may simply be manually turned by the operator using their hand. Optionally, a position sensor may be used to detect the position of the locking mechanism 952 and give feedback to the system (and/or operator) regarding its position.

FIG. 27 illustrates a PC board assembly 960 that houses the vortex chambers 226. Chamber intake ports 252 and chamber exhaust ports 254 are shown attached to the chambers 226, where flexible gas tubing is used to carry the VOC/gas mixture into and out of the chambers 226. The chamber 226 on the right side is shown in an open configuration, in order to illustrate the (optional) shutter 232 and the sensor array 234 that is mounted onto the board 960. The chamber 226 is held snugly in place, over the shutter 232 and sensor array 234, using the latch mechanism as shown on the left chamber 226. A latch 227 operates to insert a latch arm 229 into the mating latch base 231, and thus snugly lock the chamber in place onto the board 960. When it is necessary to open the chamber (e.g. to obtain access to the sensor array 234) the latch 227 is easily opened by the technician to release the latch arm 229 from the latch base 231.

Figure 28:
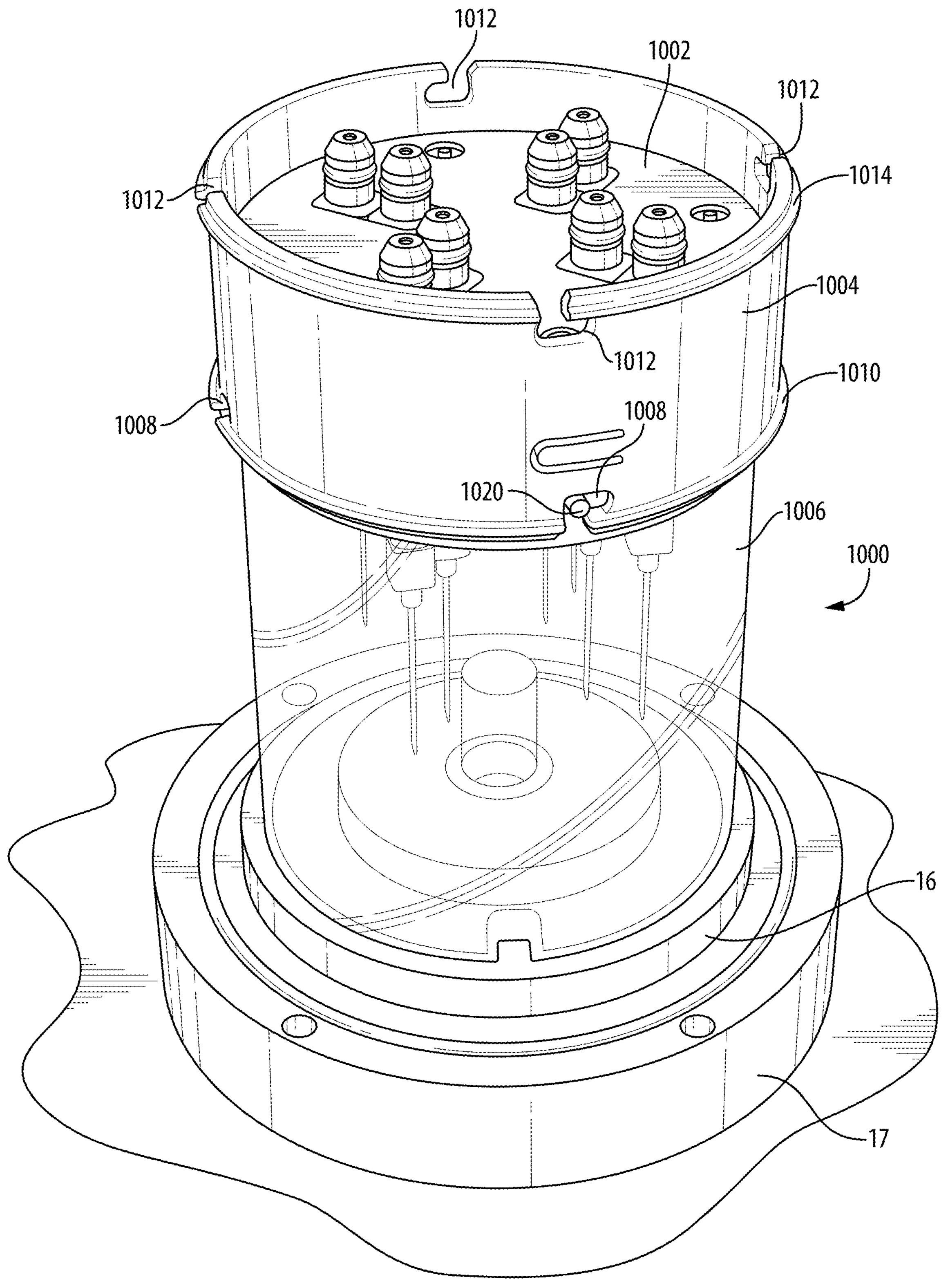
FIG. 28 is a perspective view of a needle replacement assembly.
Figure 29:
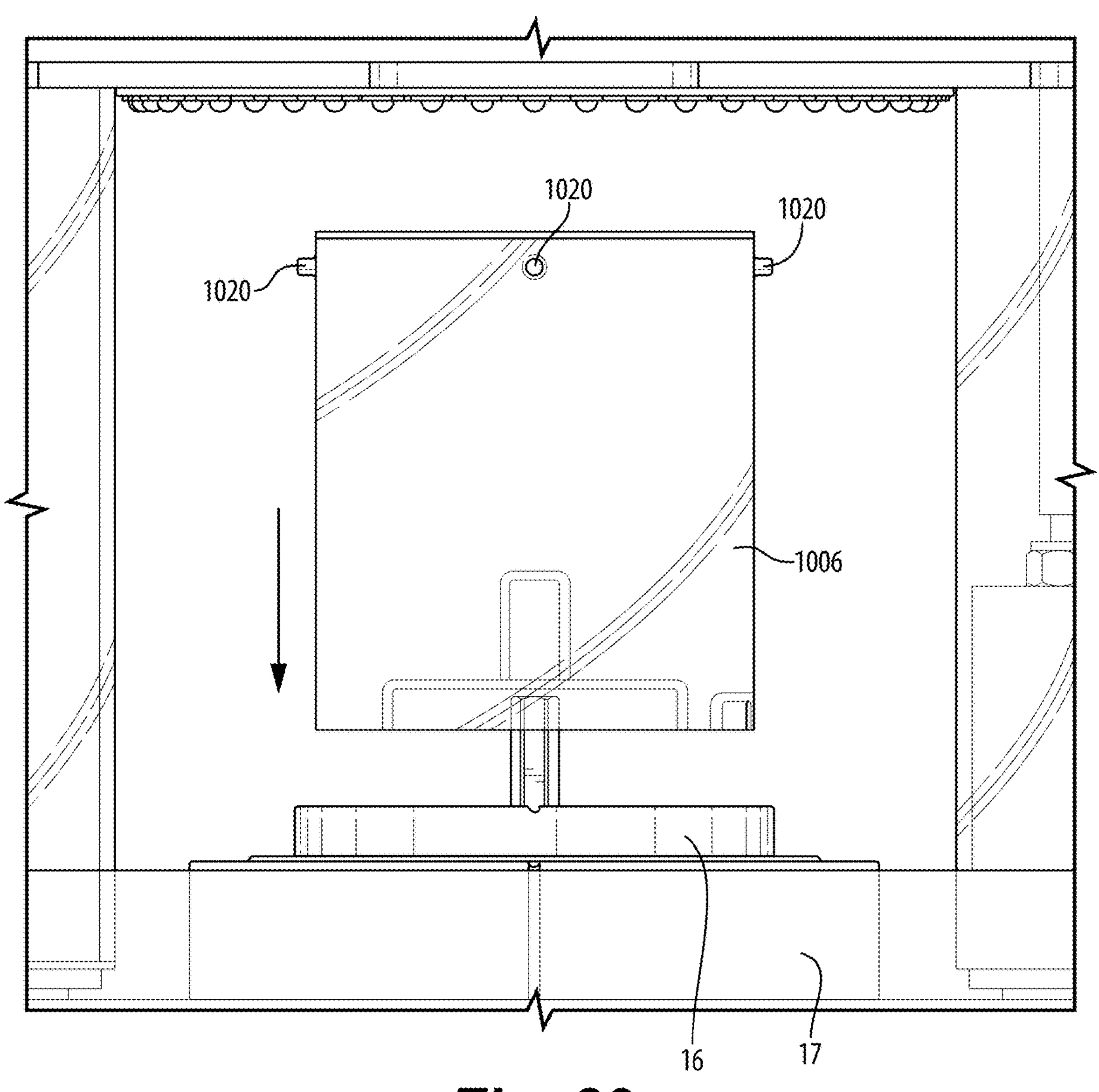
FIG. 29 is an illustration of a cup being lowered onto the vial block mount located in the testing area of the apparatus.
Figure 30:
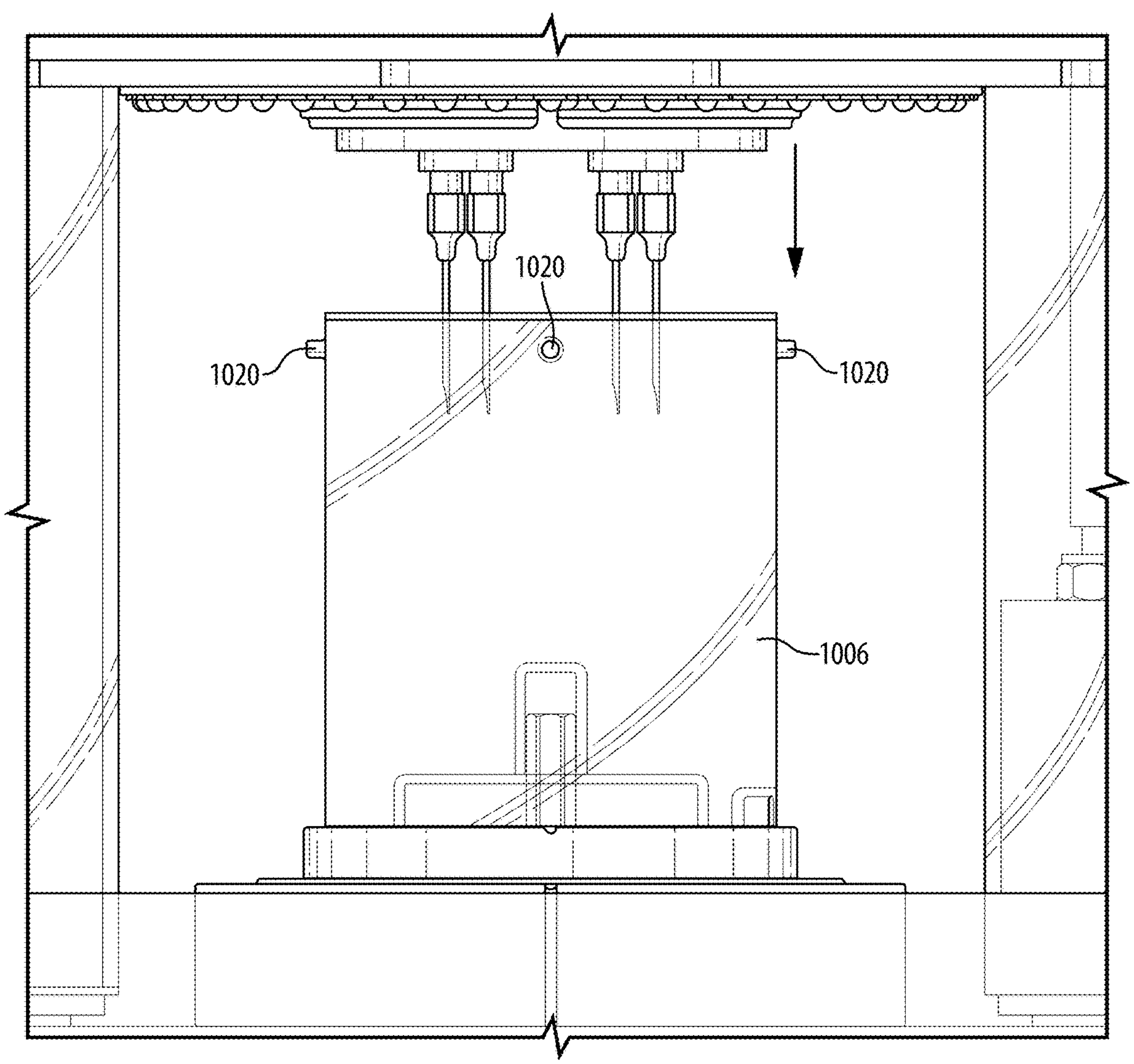
FIG. 30 illustrates the cup located onto the vial block mount for receiving the needles for replacement.
Figure 31:
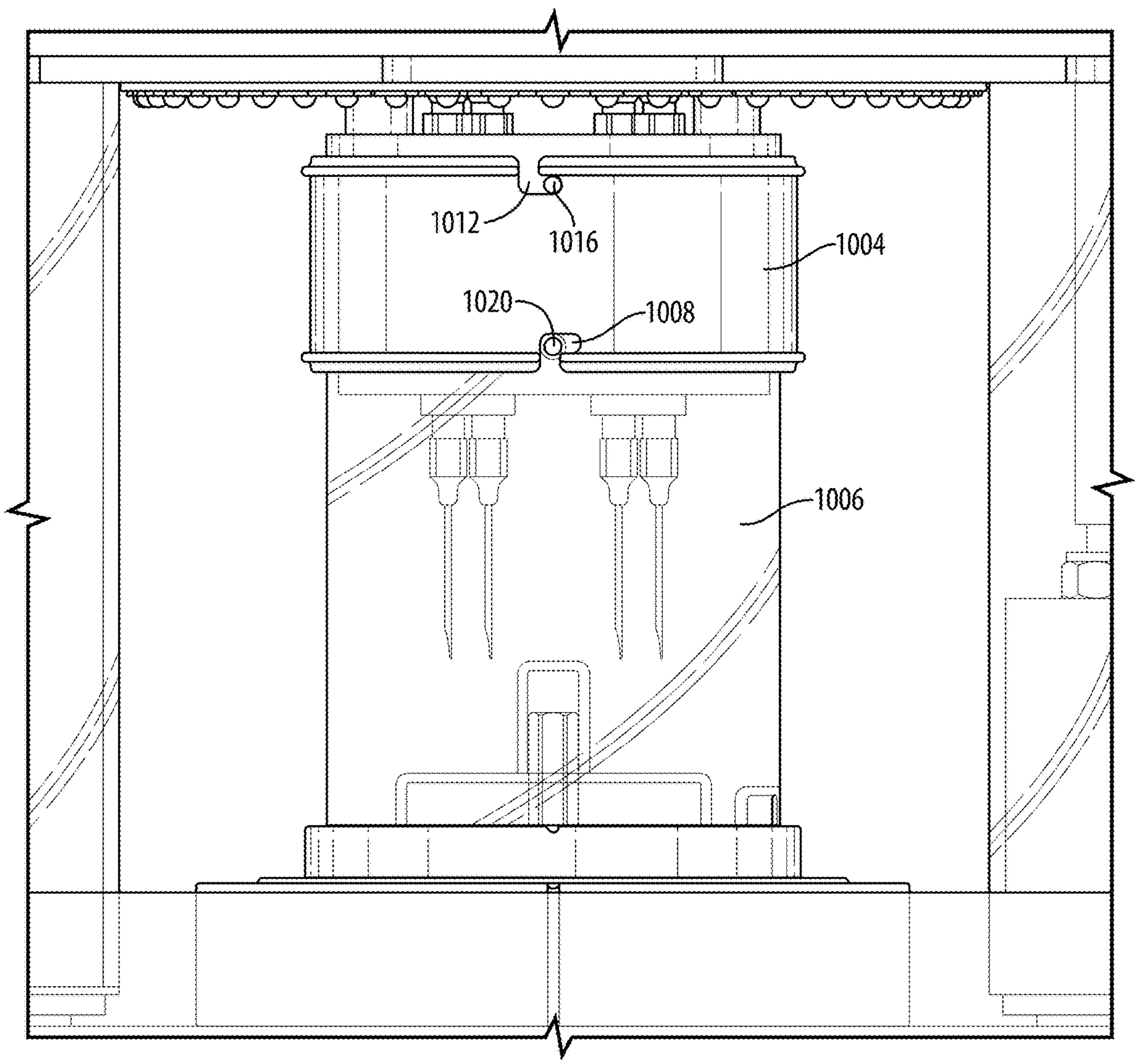
FIG. 31 illustrates the locking collar engaged with the cup.
Figure 32:
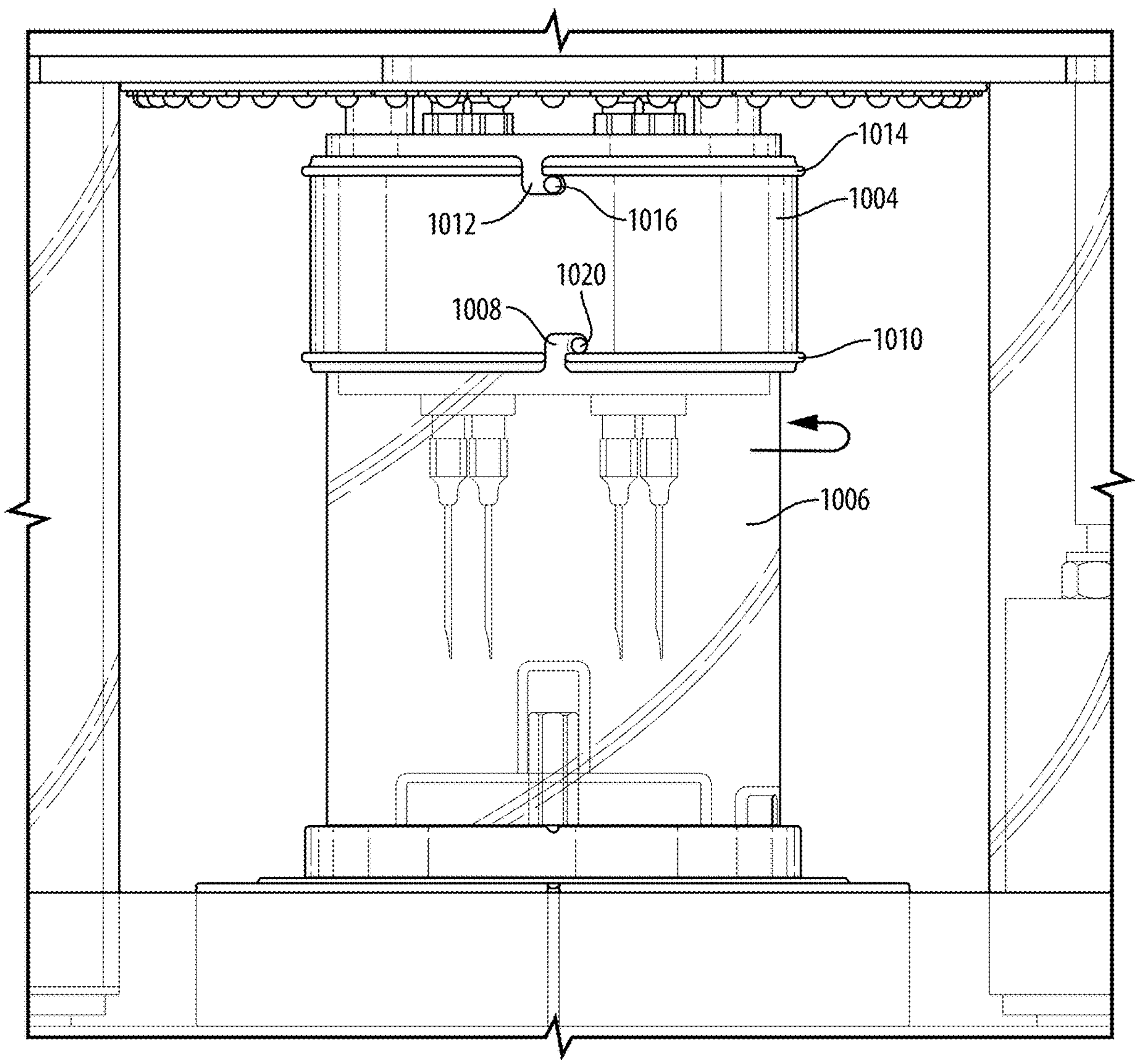
FIG. 32 illustrates alignment of the cup nubs with the lower engagement notches on the lower rim of the locking collar.
Figure 33:
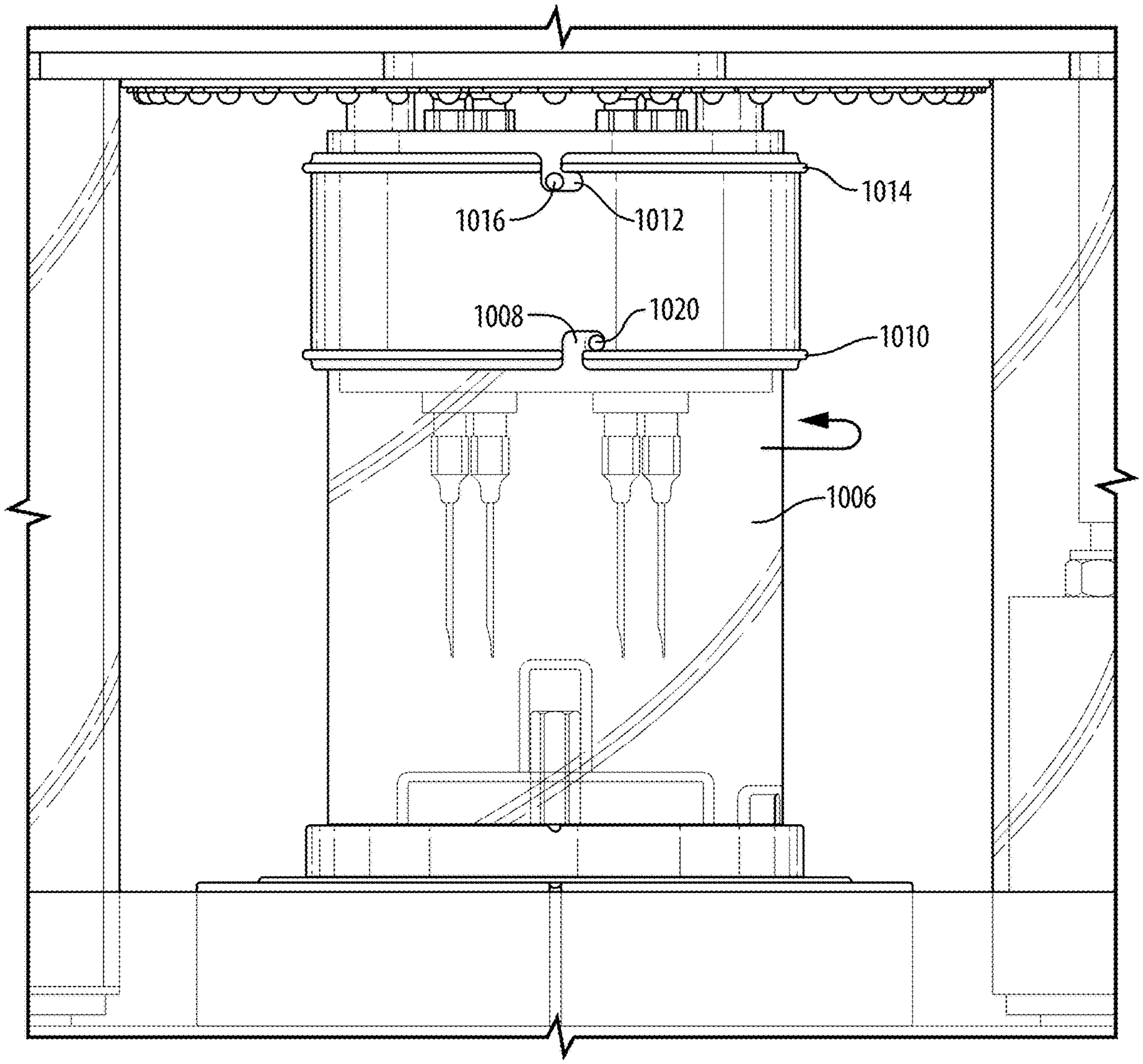
FIG. 33 illustrates the cup in rotation in a first direction with respect to the needle carrier.
Figure 34:
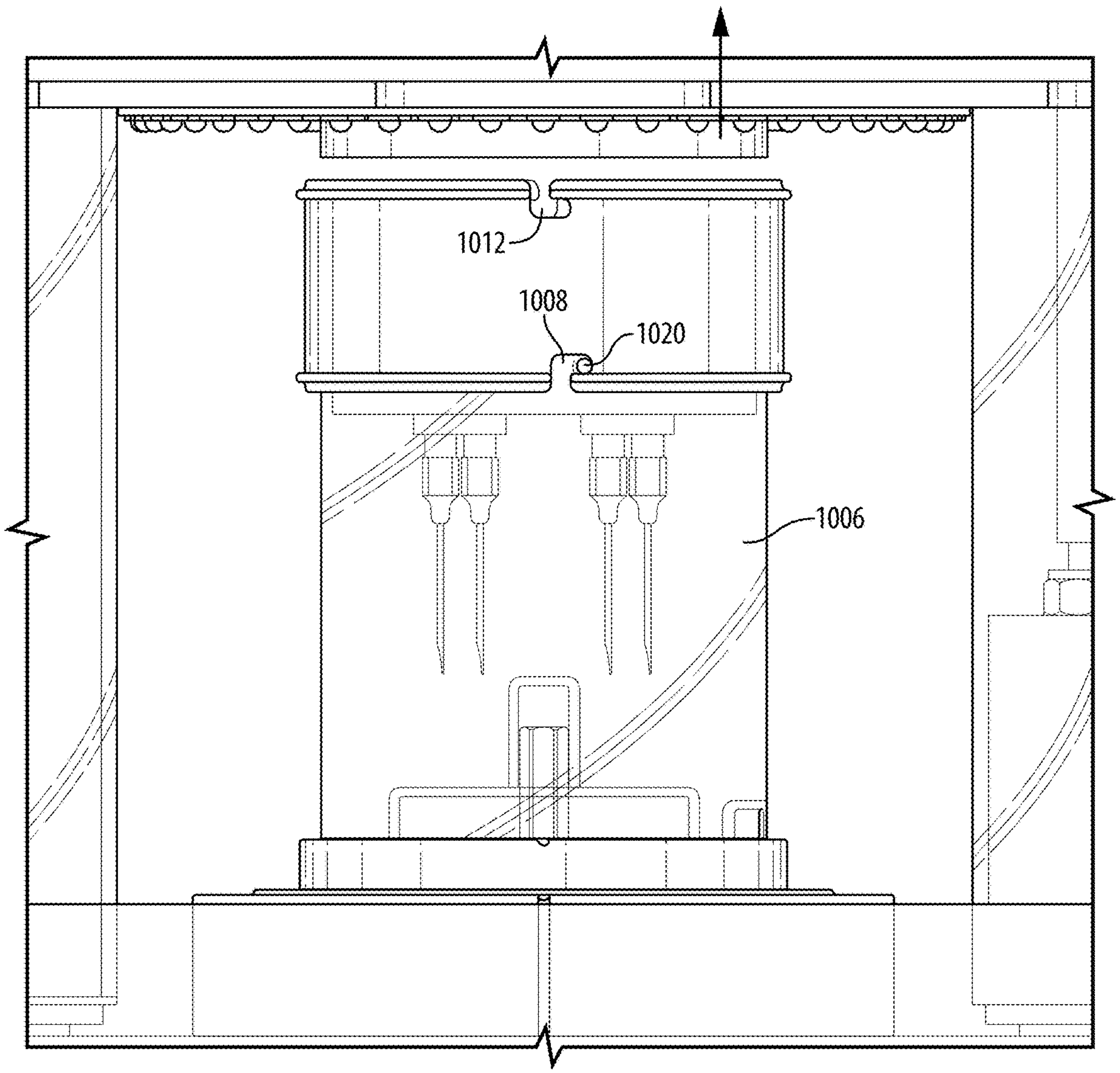
FIG. 34 illustrates upper engagement notches disengaging from fixed engagement nubs, releasing the needle carrier from the apparatus.

A needle replacement assembly 1000 as shown in FIGS. 28-34 may be used to make the process of changing needles quicker and safer. The needle replacement assembly 1000 includes a cylindrical needle carrier 1002 adapted to mount the injection needle 214 and the collection needle 216 (or several pairs thereof in a multi-channel embodiment). The needle carrier 1002 has a locking collar 1004 with a plurality of lower engagement notches 1008 located around a lower rim 1010 of the locking collar 1004, and a plurality of upper engagement notches 1012 located around an upper rim 1014 of the locking collar. A cylindrical cup 1006 having a plurality of cup engagement nubs 1020 is placed under the needle carrier 1002 such that the injection needle(s) 214 and the collection needle(s) 216 are contained within the cup 1006, and the plurality of cup engagement nubs 1020 are aligned with the plurality of lower engagement notches 1008 on the lower rim 1010 of the locking collar. When the cup 1006 is rotated in a first direction with respect to the needle carrier 1002 (e.g. counter-clockwise), the cup engagement nubs 1020 engage with the lower engagement notches 1008 and cause the needle carrier 1002 to rotate such that the upper engagement notches 1012 disengage from a plurality of fixed engagement nubs 1016, releasing the needle carrier 1002 from the apparatus (FIG. 33). The needle replacement assembly 1000 as shown in FIG. 28 may now be removed from the vial block mount 16 and a new assembly 1000 placed on the vial block mount 16. The reverse process is executed so that the locking collar upper rim 104 engages with the apparatus, the lower engagement notches disengage with the associated nubs, and the cup may be removed from the apparatus. At this point, the new needles 214, 216 are fixed in place and ready to be utilized for further testing. The needle replacement assembly 1000 that has been removed may be sent to a repair facility for replacement of the individual needles as may be needed.

Figure 35:
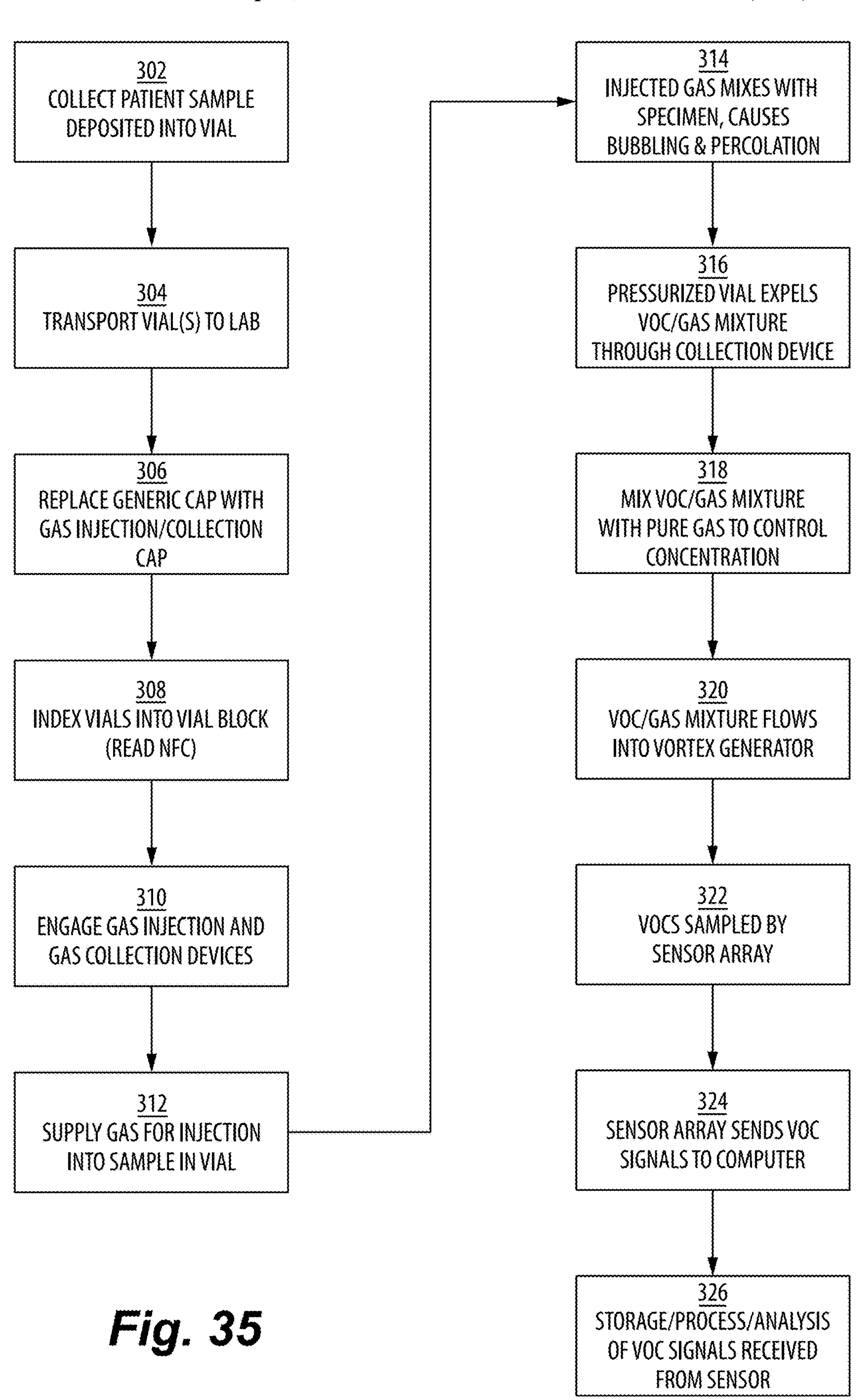
FIG. 35 is a flowchart of the overall operation of the invention.

The overall process flow is now shown with respect to the flowchart of FIG. 35. In practice, vials 24 that are ready for specimen sample collection are provided with a generic cap to the sample collection site (e.g. hospital, clinic, doctor's office etc.), and the health care provider will collect the specimen sample at step 302 and deposit the required amount into the vial, optionally sealing the vial prior to transport to the testing lab at step 304. If a bar code label is provided on the vial, it will be scanned for identification, wherein the bar code is linked to the patient for anonymous record keeping purposes. In addition or in the alternative, the NFC chip may be read for similar anonymous identification. The vial may then be provided to the testing laboratory where the apparatus of the present invention will be operated to analyze the VOCs of the specimen sample(s) provided. The testing apparatus may also be located at the site of the sample collection e.g., the hospital or clinic. On arrival at the testing facility, the bar code on the vial is scanned and optionally linked to data in the NFC chip for identification purposes, again on an anonymous basis. This will maintain the chain of custody of the vial/sample without violating the privacy of the patient.

At step 306, the generic cap is replaced by the cap 602 (for the first embodiment), cap 902 (for the second embodiment), or cap 932 (for the third embodiment). The vial is then inserted and indexed into the vial block and the NFC chip is read at step 308, and then the vials are optionally heated to a desired temperature that is conducive for percolation by the inert gas. At step 310 the gas injection device and the gas collection device are engaged with the vial, depending on which embodiment is being implemented (valves or needles). Argon gas is provided from an Argon gas supply such as the tank 104 located externally to the apparatus 10, and then fed through optional gas heaters 122, 124. At step 312 the gas is supplied to the gas injection device 20 and into the specimen samples in the vial 24, which have been optionally preheated with the flexible heating strip located on the vial block mount in which the vials are placed. At step 314, the liquid specimen sample percolates with the heated gas, bubbles up and releases the VOCs that are captured at step 316 by the gas collection device 22 in the headspace of the vial. Percolation of the gas is an important aspect of this invention in order to assist the release of the VOCs from the specimen sample. At step 318, the VOC/gas mixture is mixed with a supply of pure gas to optionally vary the concentration of the VOCs in the mixture. At step 320, the VOC/gas mixture is fed into the vortex chamber 226. At step 322, VOCs are sampled by the sensor arrays, which sends VOC signals at step 324 to the processing board circuitry. At step 326, the VOC signals received from sensors undergo storage, processing and analysis.

As previously explained, in one embodiment, four vials containing four different specimens may be inserted into the vial block, and the four independent measurement channels are then used to extract the VOCs and generate four separate electrical signals, one for each vial placed in the vial block. In this embodiment, specimens may be processed in parallel, at approximately four times the speed of a single vial processed by each of the four measurement channels.

Figure 36:
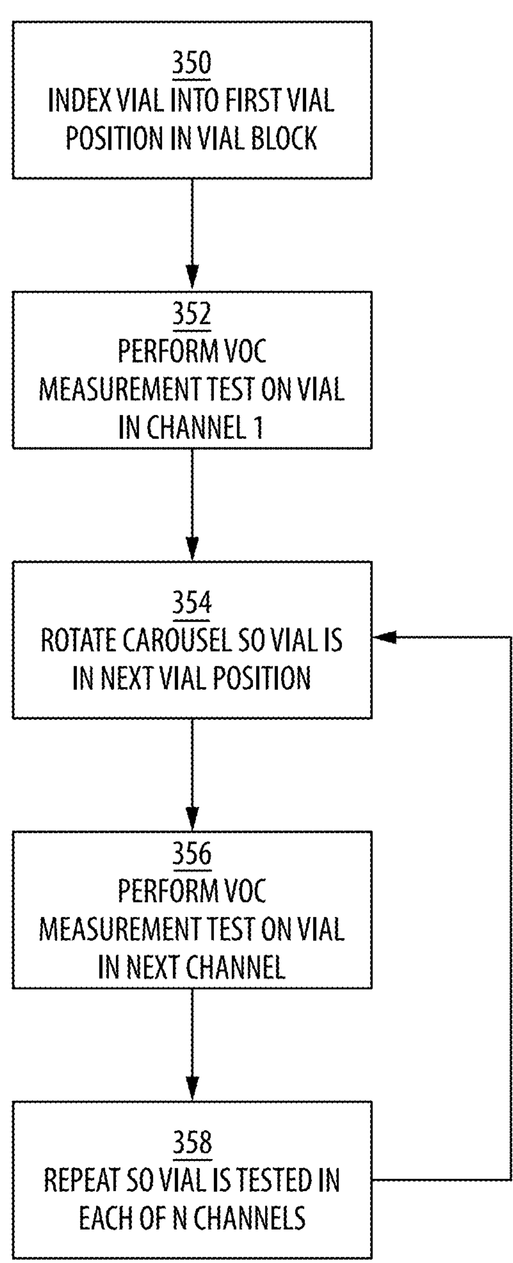
FIG. 36 is a flowchart of the operation of an alternative operation of the invention.

In another embodiment, with reference to the flowchart of FIG. 36, a single vial may be placed in the vial block, which may be rotated around by the carousel to be sampled by each of the four channels in succession. In this manner, four times as much data is obtained for a single specimen than would otherwise be available with only a single channel. In this case, at step 350 the vial is indexed and placed into the first position in the vial block. The VOC measurement test is then carried out on that vial in the first measurement channel at step 352. The carousel is then rotated at step 354 so that the vial is located in the next position, and at step 356 the VOC measurement test is then carried out on that vial in the next measurement channel. This process repeats at step 358 so that the vial specimen is tested for each of the n channels in the apparatus, which in the preferred embodiment is four.

In an alternative embodiment, it is not necessary to provide an inert gas supply to inject into the vial, since the VOCs present in the specimen may naturally disperse into the headspace over the specimen. In that case, the VOC/gas mixture (the gas likely being air) can be caused to enter the chamber for analysis by the sensor array by de-pressurizing the headspace above the specimen in the vial to cause it to flow into the chamber. As such, this method for determining the presence of a disease by analyzing a specimen using an apparatus, includes the steps of providing in the apparatus a vial partially containing the specimen and partially containing a headspace above the specimen, de-pressurizing the headspace in the vial, collecting a VOC/gas mixture from the headspace in the vial, supplying the VOC/gas mixture to a chamber within the apparatus, causing the VOC/gas mixture to pass over a sensor array in proximity to the chamber, the sensor array generating an electrical signal as a function of VOCs detected in the VOC/gas mixture, and processing the electrical signal to determine the presence of a disease in the specimen. Here, the step of de-pressurizing the headspace in the vial comprises coupling a pneumatic cylinder to an exit port of the chamber and operating the pneumatic cylinder to de-pressurize the headspace in the vial.

This alternative embodiment apparatus for determining the presence of a disease by analyzing a specimen, includes a housing, a vial partially containing the specimen and partially containing a headspace above the specimen, a gas collection device adapted to collect a VOC/gas mixture from the headspace in the vial and feed the VOC/gas mixture to a chamber, a pneumatic cylinder coupled to an exit port of the chamber, the pneumatic cylinder operable to de-pressurize the headspace in the vial, a system controller computer connected to the pneumatic cylinder, the system controller programmed to control de-pressurization of the headspace in the vial, and a printed circuit board comprising a sensor array in proximity to the chamber, the chamber coupled to the output of the gas collection device, such that the VOC/gas mixture output by the gas collection device passes over the sensor array, the sensor array generating an electrical signal as a function of VOCs detected in the VOC/gas mixture, the system controller further programmed to process the electrical signal to determine the presence of a disease in the specimen.

What is claimed is:

1. A method of determining the presence of a disease by analyzing a specimen using an apparatus, comprising the steps of:

providing in the apparatus a vial partially containing the specimen and partially containing a headspace above the specimen;

injecting a gas into the specimen in the vial, to cause bubbling of the gas throughout at least a portion of the specimen such that the gas mixes with volatile organic compounds (VOCs) present in the specimen to create a VOC/gas mixture that is released into the headspace collecting the VOC/gas mixture from the headspace in the vial;

supplying the VOC/gas mixture to a chamber within the apparatus;

controlling pressure within the chamber with a pneumatic cylinder coupled to the chamber to control the supply of the VOC/gas mixture through the chamber;

the VOC/gas mixture passing over a sensor array in proximity to the chamber;

the sensor array generating an electrical signal related to VOCs detected in the VOC/gas mixture;

comparing the electrical signal to a library of stored VOC signatures, each of the stored VOC signatures associated with a disease, to determine the presence of a disease in the specimen.

2. The method of claim 1 wherein, prior to injecting a gas into the specimen in the vial, the gas flows through a first mass flow controller within the apparatus, the first mass flow controller providing control of the flow rate of the gas injected into the vial.

3. The method of claim 2 further comprising the steps of dividing the flow of gas into two paths comprising:

a first path that couples to the first mass flow controller, and a second path that couples to a second mass flow controller, mixing an output of the second mass flow controller with the VOC/gas mixture collected from the vial prior to being supplied to the chamber; and operating the first mass flow controller and the second mass flow controller to control the mixing of the output of the second mass flow controller relative to the VOC/gas mixture collected from the vial prior to being supplied to the chamber;

whereby the concentration of VOCs being supplied to the chamber may be selectively controlled.

4. The method of claim 1 further comprising the steps of providing a shutter between the chamber and the sensor array, and operating the shutter to control flow of the VOC/gas mixture within the chamber to the sensor array.

5. The method of claim 1 wherein the vial comprises a removable vial cap comprising a gas injection valve, a gas input passageway coupled to a first side of the gas injection valve and an injection passageway coupled to a second side of the gas injection valve, the injection passageway comprising an opening extending through the headspace and into the specimen, a gas collection valve, and a gas output passageway coupled to a first side of the gas collection valve and a collection passageway coupled to a second side of the gas collection valve, the collection passageway coupled to the headspace and not extending into the specimen;

wherein:

the step of injecting a gas into the specimen in the vial, to cause bubbling of the gas throughout at least a portion of the specimen such that the gas mixes with volatile organic compounds (VOCs) present in the specimen to create a VOC/gas mixture that is released into the headspace, comprises:

inserting an injection tube into the gas input passageway to make contact with the first side of the gas injection valve and cause the gas injection valve to open, and injecting the gas via the open gas injection valve and through the opening into the specimen; and the step of collecting the VOC/gas mixture from the headspace in the vial comprises:

inserting a collection tube into the gas output passageway to make contact with the first side of the gas collection valve and cause the gas collection valve to open, and collecting the VOC/gas mixture from the headspace via the open gas collection valve.

6. The method of claim 5 wherein the injection passageway comprises a multiplicity of openings located throughout a portion of the injection passageway that extends into the specimen, whereby the gas injected via the open gas injection valve passes through the multiplicity of openings into the specimen, causing a micro-bubbling of the gas within the specimen that results in the VOC/gas mixture.

7. The method of claim 1 wherein the vial comprises a removable vial cap comprising a penetrable membrane and an injection passageway comprising at least one injection passageway opening extending below the headspace and into the specimen, and a collection passageway adjoining the headspace and not extending into the specimen, wherein:

the step of injecting a gas into the specimen in the vial, to cause bubbling of the gas throughout at least a portion of the specimen such that the gas mixes with volatile organic compounds (VOCs) present in the specimen to create a VOC/gas mixture that is released into the headspace, comprises:

inserting an injection needle through the membrane such that a tip of the injection needle extends into the injection passageway, and injecting the gas into the specimen via the tip of the injection needle and through the at least one injection passageway opening; and the step of collecting the VOC/gas mixture from the headspace in the vial comprises:

inserting a collection needle through the membrane such that a tip of the collection needle extends into the collection passageway, and collecting the VOC/gas mixture from the headspace via the tip of the collection needle.

8. The method of claim 7 wherein the injection passageway comprises a multiplicity of openings located throughout a portion of the injection passageway that extends into the specimen, whereby the gas injected via the open gas injection valve passes through the multiplicity of openings into the specimen, causing a micro-bubbling of the gas within the specimen that results in the VOC/gas mixture.

9. The method of claim 1 wherein the vial comprises a removable vial cap comprising a penetrable membrane;

wherein:

the step of injecting a gas into the specimen in the vial, to cause bubbling of the gas throughout at least a portion of the specimen such that the gas mixes with volatile organic compounds (VOCs) present in the specimen to create a VOC/gas mixture that is released into the headspace, comprises:

inserting an injection needle through the membrane such that a tip of the injection needle extends below the headspace and into the specimen, and injecting the gas into the specimen via the tip of the injection needle; and the step of collecting the VOC/gas mixture from the headspace in the vial comprises:

inserting a collection needle through the membrane such that a tip of the collection needle extends into the headspace and not extending into the specimen, and collecting the VOC/gas mixture from the headspace via the tip of the collection needle.

10. An apparatus for determining the presence of a disease by analyzing a specimen, comprising:

a vial partially containing the specimen and partially containing a headspace above the specimen;

means for injecting a gas into the specimen in the vial to cause bubbling of the gas throughout at least a portion of the specimen such that the gas mixes with volatile organic compounds (VOCs) present in the specimen to create a VOC/gas mixture that is released into the headspace;

a printed circuit board comprising a sensor array in proximity to a chamber;

means for collecting the VOC/gas mixture from the headspace in the vial and supplying the VOC/gas mixture to the chamber;

a pneumatic cylinder coupled to the chamber;

a system controller computer connected to the pneumatic cylinder, the system controller programmed to control the pneumatic cylinder to control pressure within the chamber to control the supply of the VOC/gas mixture through the chamber wherein the VOC/gas mixture in the chamber passes over the sensor array, the sensor array generating an electrical signal as a function of VOCs detected in the VOC/gas mixture;

wherein the system controller is further programmed to compare the electrical signal to a library of stored VOC signatures, each of the stored VOC signatures associated with a disease to determine the presence of a disease in the specimen.

11. The apparatus of claim 10 further comprising a housing;

a gas input valve for interconnecting a supply of gas to the housing;

a manifold adapted to divide a supply of gas input via the gas input valve into a first gas line supplied to a first mass flow controller and a second gas line supplied to a second mass flow controller;

a first mass flow controller coupled to the first gas line output from the manifold;

a second mass flow controller coupled to the second gas line output from the manifold; and a mixing tee, comprising an output coupled to the chamber, for mixing the VOC/gas mixture from the gas collection device with gas received from an output of the second mass flow controller;

wherein the system controller computer is further connected to the first mass flow controller and the second mass flow controller and is further programmed to control a flow rate of the gas through the first mass flow controller and a flow rate of the gas through the second mass flow controller in order to control the concentration of VOCs being supplied to the chamber by the output of the mixing tee.

12. The apparatus of claim 10 further comprising a shutter between the chamber and the sensor array, operated to control flow of the VOC/gas mixture within the chamber to the sensor array.

13. The apparatus of claim 10 wherein the means for injecting a gas into the specimen in the vial to cause bubbling of the gas throughout at least a portion of the specimen such that the gas mixes with volatile organic compounds (VOCs) present in the specimen to create a VOC/gas mixture that is released into the headspace comprises a gas injection device, comprising:

a vial cap removably coupled to the vial, the vial cap comprising a gas injection valve, and a gas input passageway coupled to a first side of the gas injection valve and an injection passageway coupled to a second side of the gas injection valve, the injection passageway comprising an opening extending through the headspace and into the specimen, and an injection tube coupled to the output of a first mass flow controller, whereby, when the injection tube is inserted into the gas input passageway and makes contact with and urges against the first side of the gas injection valve, the gas injection valve is caused to open and the gas is injected into the specimen via the open gas injection valve and through the at least one opening, causing gas provided from the first mass flow controller to bubble throughout at least a portion of the specimen; and wherein the means for collecting the VOC/gas mixture from the headspace in the vial and supplying the VOC/gas mixture to the chamber comprises a gas collection device comprising a gas collection valve in the vial cap, a gas output passageway in the vial cap and coupled to a first side of the gas collection valve, a collection passageway in the vial cap coupled to a second side of the gas collection valve, the collection passageway adjoining the headspace and not extending into the specimen, and a collection tube coupled to a first input of a mixing tee;

whereby, when the collection tube is inserted into the gas output passageway and makes contact with and urges against the first side of the gas collection valve, the gas collection valve is caused to open and the VOC/gas mixture is collected from the headspace via the open gas collection valve.

14. The apparatus of claim 13 wherein the injection passageway comprises a multiplicity of openings located throughout a portion of the injection passageway that extends into the specimen, whereby the gas injected via the open gas injection valve passes through the multiplicity of openings into the specimen, causing a micro-bubbling of the gas within the specimen that results in the VOC/gas mixture.

15. The apparatus of claim 10 wherein the means for injecting a gas into the specimen in the vial to cause bubbling of the gas throughout at least a portion of the specimen such that the gas mixes with volatile organic compounds (VOCs) present in the specimen to create a VOC/gas mixture that is released into the headspace comprises a gas injection device, comprising:

a vial cap removably coupled to the vial, the vial cap comprising:

a penetrable membrane, and an injection passageway comprising at least one injection passageway opening extending below the headspace and into the specimen, and an injection needle insertable through the membrane such that a tip of the injection needle extends into the injection passageway;

whereby gas is injected into the specimen via the tip of the injection needle and through the at least one injection passageway opening;

and wherein the means for collecting the VOC/gas mixture from the headspace in the vial and supplying the VOC/gas mixture to the chamber comprises a gas collection device comprising a collection passageway in the vial cap adjoining the headspace and not extending into the specimen, and a collection needle insertable through the membrane such that a tip of the collection needle extends into the collection passageway, whereby the VOC/gas mixture is collected from the headspace via the tip of the collection needle.

16. The apparatus of claim 15 further comprising a needle replacement assembly comprising:

a cylindrical needle carrier adapted to mount the injection needle and the collection needle, the needle carrier comprising a locking collar comprising a plurality of lower engagement notches located around a lower rim of the locking collar, and a plurality of upper engagement notches located around an upper rim of the locking collar; and a cylindrical cup comprising a plurality of cup engagement nubs;

whereby, when the cup is located under the needle carrier such that the injection needle and the collection needle are contained within the cup, and the plurality of cup engagement nubs are aligned with the plurality of lower engagement notches on the lower rim of the locking collar, and the cup is rotated in a first direction with respect to the needle carrier, the cup engagement nubs engage with the lower engagement notches and cause the needle carrier to rotate such that the upper engagement notches disengage from a plurality of fixed engagement nubs, releasing the needle carrier from the apparatus.

17. The apparatus of claim 10 wherein the means for injecting a gas into the specimen in the vial to cause bubbling of the gas throughout at least a portion of the specimen such that the gas mixes with volatile organic compounds (VOCs) present in the specimen to create a VOC/gas mixture that is released into the headspace comprises a gas injection device, comprising:

a vial cap removably coupled to the vial, the vial cap comprising a penetrable membrane, and an injection needle insertable through the membrane such that a tip of the injection needle extends below the headspace and into the specimen;

whereby gas is injected into the specimen via the tip of the injection needle;

and wherein the means for collecting the VOC/gas mixture from the headspace in the vial and supplying the VOC/gas mixture to the chamber comprises a gas collection device comprising a collection needle insertable through the membrane such that a tip of the collection needle extends the headspace and not into the specimen;

whereby the VOC/gas mixture is collected from the headspace via the tip of the collection needle.

18. The apparatus of claim 17 further comprising a needle replacement assembly comprising:

a cylindrical needle carrier adapted to mount the injection needle and the collection needle, the needle carrier comprising a locking collar comprising a plurality of lower engagement notches located around a lower rim of the locking collar, and a plurality of upper engagement notches located around an upper rim of the locking collar; and a cylindrical cup comprising a plurality of cup engagement nubs;

whereby, when the cup is located under the needle carrier such that the injection needle and the collection needle are contained within the cup, and the plurality of cup engagement nubs are aligned with the plurality of lower engagement notches on the lower rim of the locking collar, and the cup is rotated in a first direction with respect to the needle carrier, the cup engagement nubs engage with the lower engagement notches and cause the needle carrier to rotate such that the upper engagement notches disengage from a plurality of fixed engagement nubs, releasing the needle carrier from the apparatus.

19. The apparatus of claim 15 wherein the injection passageway comprises a multiplicity of openings located throughout a portion of the injection passageway that extends into the specimen, whereby the gas injected via the open gas injection valve passes through the multiplicity of openings into the specimen, causing a micro-bubbling of the gas within the specimen that results in the VOC/gas mixture.

* * * * *